US005096823A

United States Patent [19]

Gloeckler et al.

[11] Patent Number: 5,096,823

[45] Date of Patent: Mar. 17, 1992

[54] CLONING OF THE BIOA, BIOD, BIOF, BIOC AND BIOH GENES OF BACILLUS SPRAERICUS, VECTORS AND TRANSFORMED CELLS

[75] Inventors: Rémi Gloeckler, Strasbourg; Denis Speck, Eckbolsheim; Yves Lemoine, Strasbourg-Neudorf, all of France

[73] Assignee: Transgene S.A., Courbevoie, France

[21] Appl. No.: 102,740

[22] Filed: Sep. 30, 1987

[30] Foreign Application Priority Data

Sep. 30, 1986 [FR] France ................................ 8613603
May 18, 1987 [FR] France ................................ 8706916

[51] Int. Cl.$^5$ ...................... C12N 15/31; C12N 15/52; C12N 15/63; C12N 1/21

[52] U.S. Cl. ............................ 435/252.31; 435/252.3; 435/252.33; 435/172.3; 435/320.1; 435/119; 536/27

[58] Field of Search ..................... 435/172.3, 119, 320, 435/252.3, 252.31, 252.33, 320.1; 536/27

[56] References Cited

FOREIGN PATENT DOCUMENTS

WO87/0391 3/1987 PCT Int'l Appl. .

OTHER PUBLICATIONS

J. P. Watson et al., *Molecular Biology of the Gene*, p. 205, 4th Edition, 1987.

Mountain et al., Cloning of a *Bacillus sellis* restrictor fragment complementary autotophic mutants of eight *E. coli* genes of org. biosyn., MGG 197: 82-89, 1984.

Gupta et al.; Elsevier/North-Holland Biomedical Press, Gene, vol. 1, 1977, pp. 331-345; Isolation & Characterization of the Biotin Genes of Escherichia Coli K-12.

Izumi et al.; Agri. Biol. Chem., vol. 45, No. 9, 1981, pp. 1983-1989; Characterization of Biotin Biosxynthetic Enzymes of *Bacillus Sphaericus:* A Dethiobiotin Producing Bacterium.

Sancar et al.; J. Mol. Biol., vol. 148, 1981, pp. 63-76; Identification of the UVR B Gene Product.

Chemical Abstract; vol. 93, No. 7, Aug. 18, 1980; p. 480; Construction and Characterization of a Recombinant Plasmid Containing . . . Genes of E. Coli K12.

Chemical Abstracts; vol. 90, No. 9, Feb. 26, 1979, p. 250; Isolation and Characterization of a ColE1 Plasmid Containing the Entire Bio Gene Cluster of Escherichia Coli K12.

Chemical Abstracts; vol. 106, No. 3, Jan. 19, 1987; p. 209; Recombinant Plasmids Containing Biotin Synthetase Gene.

*Primary Examiner*—Richard A. Schwartz
*Assistant Examiner*—S. L. Nolan
*Attorney, Agent, or Firm*—Cushman, Darby & Cushman

[57] ABSTRACT

The present invention relates, in particular, to a DNA sequence corresponding to one of the following genes involved in the chain of biotin biosynthesis in bacteria: bioA gene, bioD gene, bioF, bioC and bioH gene.

Vectors containing these sequences enable other microorganisms to be transformed in order to improve the production of biotin.

21 Claims, 38 Drawing Sheets

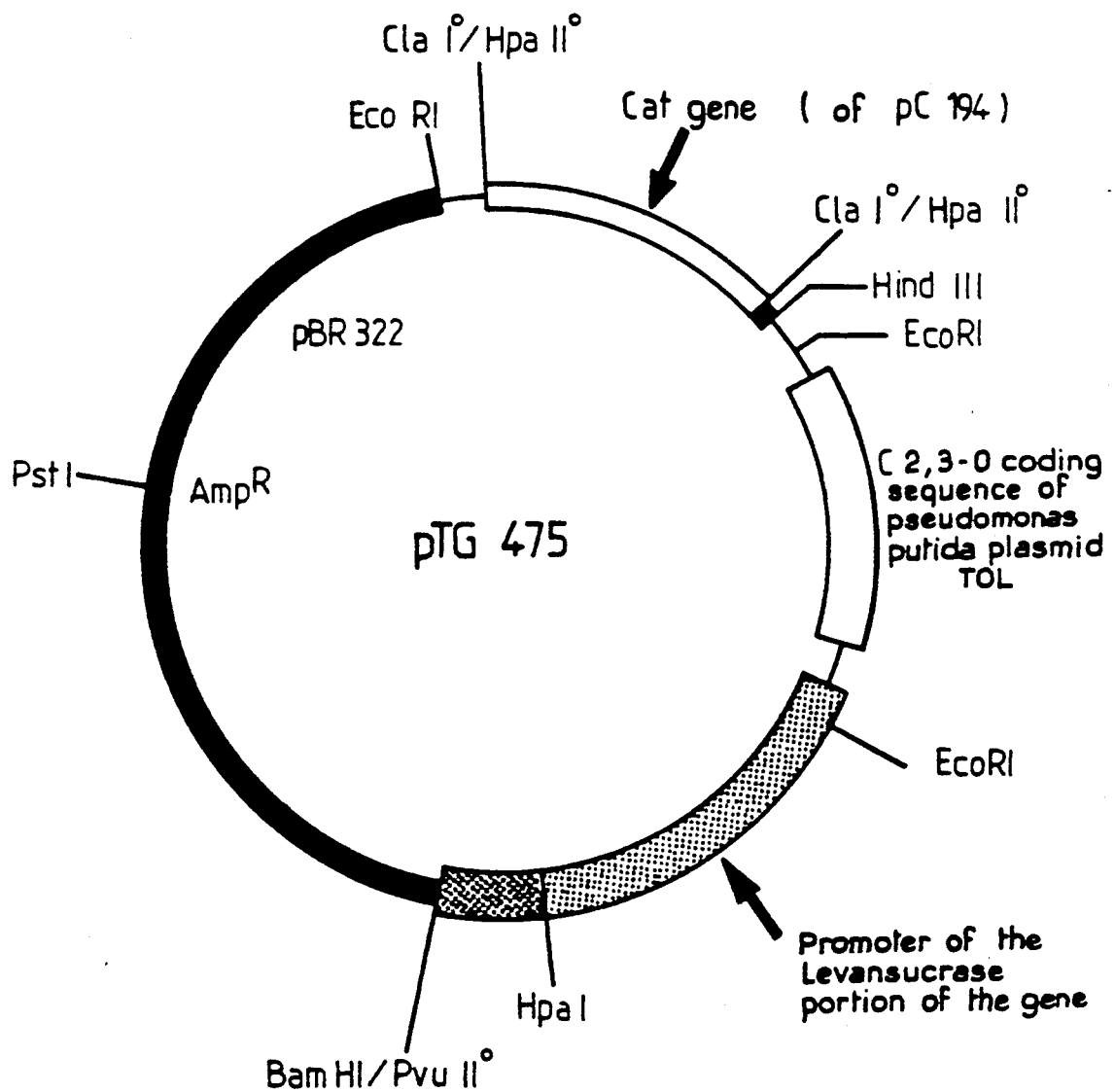

FIG. 4

```
         10         20         30         40         50
     AAGCTTTGCA CACTTCTGTT TCGTATCCTC ATATTGAACT TGATGAAACC 60         70         80         90        100
     TTCCTATGGC CGTATGCATT GAGATTTTTT CTCGATGTTC TGCTTGCAAT 110        120        130        140        150
     GTTCGATATT CTTCTTGCCG AATAGCTACA CGATACCAAA ATTCATAACG 160        170        180        190        200
     CAACGGTAAA TCTCTTATTT CGTAAGTAAG CAAAGTATTT AAAATACTGC 210        220        230        240        250
     TCATTTGTTC ATATGTATCT AGCTTTTTAT CTGTCTCCTT AAATAGTCCA 260        270        280        290        300
     AACATTTTGC CACCCCTGT TTTGATTAAT ACTACAACCT ATGATAAAAA 310        320        330        340        350
     CCCTTTAATA TTTCTTGGGA AATAATCCAA CGTTGATAAA ACGGGGTGAA 360        370        380        390        400
     TATCCGATCA ATCGAGTGAA ATTTAGGATA GAATACCCTC GGAAAAAGCA 410        420        430        440        450
     TTATCTGAAT CATTTATGTA AAAATGCAAA AAAAGGCATT TACAAAAGGA 460        470        480
               AAAAGAATGT GTTAACTTAA AAACTATAGT             TGGTT
```

FIG. 5

AAAAAGAATGTGTTAACTTAAAAACTATAGTTGGT

485          RBS
```
    TAA CTA AAA GAG GGG GAG GTA CAG TTG  CAA
    zzz Leu Lys Glu Gly Glu Val Gln Leu Gln
```

515
```
    CAC TTT TGG GTT GTT GGA ACA GAT ACA GAT
    His Phe Trp Val Val Gly Thr Asp Thr Asp
```

545
```
    GTT GGA AAA ACA TTT GTC ACC ACA TTA TTA
    Val Gly Lys Thr Phe Val Thr Thr Leu Leu
```

575
```
    ATG  CGT AAT TTG  CAA AAA CAG GGC GTA CGT
    Met Arg Asn Leu Gln Lys Gln Gly Val Arg
```

605
```
    GTA ACG CCT TAT AAA CCA GTC CAA ACT GGT
    Val Thr Pro Tyr Lys Pro Val Gln Thr Gly
```

635
```
    GAA GTG TAT GAT GGT GAA CAA GCC TAT TAC
    Glu Val Tyr Asp Gly Glu Gln Ala Tyr Tyr
```

665
```
    TTC GAC ACA GCG ATG TAT GAA AAA TAT TCC
    Phe Asp Thr Ala Met Tyr Glu Lys Tyr Ser
```

695
```
    TTG CAA TTG CTA GAC AGA GAG AAT TTA AAT
    Leu Gln Leu Leu Asp Arg Glu Asn Leu Asn
```

725
```
    GGC TAT TCA TTT AAA GAG GCT GCA TCG CCA
    Gly Tyr Ser Phe Lys Glu Ala Ala Ser Pro
```

755
```
    CAT TTT GCG GCT CAA CTG GAG GGG CAG CAA
    His Phe Ala Ala Gln Leu Glu Gly Gln Gln
```

FIG. 5 (CONT'D)-1

785
ATT GAC ACA CAG CAG TTA TTA AAG CAA ATG
Ile Asp Thr Gln Gln Leu Leu Lys Gln Met

815
CAA CTT TTA CAG CAA ACA TGG GAT GTT GTT
Gln Leu Leu Gln Gln Thr Trp Asp Val Val

845
ATT TGT GAA GGA GCG GGT GGG CTC TTT GTG
Ile Cys Glu Gly Ala Gly Gly Leu Phe Val

875
CCA TTA GAT GCA TGT GGC GAA ACG ACA TTG
Pro Leu Asp Ala Cys Gly Glu Thr Thr Leu

905
TTG GAT GTC ATT GTT GAA AGT AAA CTA CCC
Leu Asp Val Ile Val Glu Ser Lys Leu Pro

935
GTT GTC GTG GTT ACA CGA ACA GCA CTA GGA
Val Val Val Val Thr Arg Thr Ala Leu Gly

965
ACA ATT AAC CAT ACG CTC TTA ACG TTA GAG
Thr Ile Asn His Thr Leu Leu Thr Leu Glu

995
GCA TTG ACT ACA CGG AAA ATT GAA GTG CTT
Ala Leu Thr Thr Arg Lys Ile Glu Val Leu

FIG. 5 (CONT'D)-2

```
1025
    GGT CTT GTA TTT AAC GGT GAT ATG GGG AGC
    Gly Leu Val Phe Asn Gly Asp Met Gly Ser

1055
    AGG ATG GAG CAA GAC AAT ATC CAA ACG ATT
    Arg Met Glu Gln Asp Asn Ile Gln Thr Ile

1085
    TTA CAG TAT TAT ACA TTG CCC TAT ATG ACG
    Leu Gln Tyr Tyr Thr Leu Pro Tyr Met Thr

1115
    ATA CCA AAG CTG GAA GAG CTG TCG GAC ATT
    Ile Pro Lys Leu Glu Glu Leu Ser Asp Ile

1145
    AAT GAG TAT GCA ATT ACG GGC ACA TCA TTG
    Asn Glu Tyr Ala Ile Thr Gly Thr Ser Leu

1175
    TTT GAA AGG CTG ATT AGA CGT GAA ACA AGT
    Phe Glu Arg Leu Ile Arg Arg Glu Thr Ser

1205
    ATT AAC TGA GCT ACA AGA
    Ile Asn zzz

1235
                           AAA AGA TTT ACA ACA TGT
```

FIG. 6

GTATGCAATTACGGGCACATCATTGTTTGAAAGGC

1185
```
TGA TTA GAC GTG AAA CAA GTA TTA ACT GAG
zzz Leu Asp Val Lys Gln Val Leu Thr Glu
```

1215
```
CTA CAA GAA AAA GAT TTA CAA CAT GTC TGG
Leu Gln Glu Lys Asp Leu Gln His Val Trp
```

1245
```
CAT CCT TGC TCA CAA ATG AAA GAT TAT GAG
His Pro Cys Ser Gln Met Lys Asp Tyr Glu
```

1275
```
GCT TTT CCA CCA ATC GTT ATA AAA AAA GGC
Ala Phe Pro Pro Ile Val Ile Lys Lys Gly
```

1305
```
GAA GGT GTA TGG CTG TAT GAT GAA CAG AAT
Glu Gly Val Trp Leu Tyr Asp Glu Gln Asn
```

1335
```
CAA CGC TAT CTT GAT GCG GTA TCT TCA TGG
Gln Arg Tyr Leu Asp Ala Val Ser Ser Trp
```

1365
```
TGG GTC AAT TTA TTT GGA CAT GCC AAT CCA
Trp Val Asn Leu Phe Gly His Ala Asn Pro
```

1395
```
CGT ATT AGC CAA GCA TTA AGT GAA CAA GCA
Arg Ile Ser Gln Ala Leu Ser Glu Gln Ala
```

1425
```
TTT ACG TTG GAG CAT ACA ATT TTT GCG AAT
Phe Thr Leu Glu His Thr Ile Phe Aln Asn
```

1455
```
TTT TCA CAT GAG CCA GCG ATT AAA CTC GCA
Phe Ser His Glu Pro Ala Ile Lys Leu Ala
```

1485
```
CAA AAA TTA GTA GCT TTA ACA CCA CAA AGT
Gln Lys Leu Val Ala Leu Thr Pro Gln Ser
```

FIG. 6 (CONT'D)-1

1515
```
    TTA CAA AAA GTA TTT TTT GCA GAT AAT GGT
    Leu Gln Lys Val Phe Phe Ala Asp Asn Gly
```

1545
```
    TCA TCT GCT ATA GAA GTC GCT TTA AAA ATG
    Ser Ser Ala Ile Glu Val Ala Leu Lys Met
```

1575
```
    AGT TTT CAA TAT CAT ATG CAA ACG GGG AAA
    Ser Phe Gln Tyr His Met Gln Thr Gly Lys
```

1605
```
    ACG CAA AAA AAA CGC TTT TTG GCA TTA ACG
    Thr Gln Lys Lys Arg Phe Leu Ala Leu Thr
```

1635
```
    GAT GCC TAC CAT GGT GAA ACA TTA GGT GCT
    Asp Ala Tyr His Gly Glu Thr Leu Gly Ala
```

1665
```
    TTA TCC GTC GGT GGC GTA GAT CTT TAT AAC
    Leu Ser Val Gly Gly Val Asp Leu Tyr Asn
```

1695
```
    GAA GTG TAT CAA CCA CTG TTA TTG GAT ACG
    Glu Val Tyr Gln Pro Leu Leu Leu Asp Thr
```

1725
```
    GTA CGA GCA CAA GGC CCA GAT TGT TTC CGT
    Val Arg Ala Gln Gly Pro Asp Cys Phe Arg
```

1755
```
    TGC CCA TTC AAG CAT CAT CCG GAT AGT TGC
    Cys Pro Phe Lys His His Pro Asp Ser Cys
```

1785
```
    CAT GCC CAA TGT ATT AGT TTT GTA GAG GAT
    His Ala Gln Cys Ile Ser Phe Val Glu Asp
```

1815
```
    CAG TTG CGC ATG CAT CAT AAG GAA ATT ACG
    Gln Leu Arg Met His His Lys Glu Ile Thr
```

1845
```
    GCG GTT ATT ATT GAG CCA CTC ATT CAA GCG
    Ala Val Ile Ile Glu Pro Leu Ile Gln Ala
```

FIG. 6 (CONT'D)-2

```
1875
    GCA GCA GGG ATG AAA ATG TAT CCA GCT ATT
    Ala Ala Gly Met Lys Met Tyr Pro Ala Ile

1905
    TAT TTG CGA CGT TTA CGT GAA CTA TGT ACG
    Tyr Leu Arg Arg Leu Arg Glu Leu Cys Thr

1935
    CAA TAT GAT GTG CAT CTA ATT GCA GAC GAA
    Gln Tyr Asp Val His Leu Ile Ala Asp Glu

1965
    ATT GCT GTA GGT TTT GGG CGC ACA GGT ACA
    Ile Ala Val Gly Phe Gly Arg Thr Gly Thr

1995
    CTT TTT GCC TGT GAG CAG GCT AAT ATC TCT
    Leu Phe Ala Cys Glu Gln Ala Asn Ile Ser

2025
    CCG GAT TTT ATG TGT TTA TCA AAA GGT TTA
    Pro Asp Phe Met Cys Leu Ser Lys Gly Leu

2055
    ACA GGT GGG TAT TTA CCA CTG TCT GTC GTA
    Thr Gly Gly Tyr Leu Pro Leu Ser Val Val

2085
    ATG ACG ACG AAT GAT GTA TAT CAG GCA TTT
    Met Thr Thr Asn Asp Val Tyr Gln Ala Phe

2115
    TAT GAT GAT TAT GCC ACG ATG AAG GCG TTT
    Tyr Asp Asp Tyr Ala Thr Met Lys Ala Phe

2145
    TTA CAT TCA CAT AGT TAC ACA GGG AAT ACA
    Leu His Ser His Ser Tyr Thr Gly Asn Thr

2175
    CTT GCC TGC CGT GTT GCT CTA GAG GTA TTG
    Leu Ala Cys Arg Val Ala Leu Glu Val Leu

2205
    GCG ATA TTT GAA GAA GAA CAG TAT ATA GAC
    Ala Ile Phe Glu Glu Glu Gln Tyr Ile Asp
```

FIG. 6 (CONT'D)-3

```
2235
    GTT GTG CAA GAC AAA GGT GAA CGC ATG CGA
    Val Val Gln Asp Lys Gly Glu Arg Met Arg

2265
    AAG CTA GCC TTG GAG GCT TTT AGT GAT TTA
    Lys Leu Ala Leu Glu Ala Phe Ser Asp Leu

2295
    CCT TTT GTT GGT GAA TAT CGG CAA GTT GGG
    Pro Phe Val Gly Glu Tyr Arg Gln Val Gly

2325
    TTT GTC GGG GCG ATT GAA CTT GTG GCG AAT
    Phe Val Gly Ala Ile Glu Leu Val Ala Asn

2355
    CGC GAT ACC AAA GAG CCA TTA CCG AGT GAG
    Arg Asp Thr Lys Glu Pro Leu Pro Ser Glu

2385
    GAG CGC ATC GGC TAT CAA ATA TAC AAA AGA
    Glu Arg Ile Gly Tyr Gln Ile Tyr Lys Arg

2415
    GCT TTA GCA AAA GGG TTA CTG ATT CGT CCA
    Ala Leu Ala Lys Gly Leu Leu Ile Arg Pro

2445
    CTT GGG AAT GTT TTG TAT TTC ATG CCA CCA
    Leu Gly Asn Val Leu Tyr Phe Met Pro Pro

2475
    TAC ATT ATA ACG GAC GAT GAA ATG CAA TTT
    Tyr Ile Ile Thr Asp Asp Glu Met Gln Phe

2505
    ATG ATT CAA ACA ACA AAA GAT ACA ATT GTT
    Met Ile Gln Thr Thr Lys Asp Thr Ile Val

2535
    CAA TTT TTT GAA GAG CGG GAG GGA TGA GGG
    Gln Phe Phe Glu Glu Arg Glu Gly zzz 2565                                              2595
    CAT GTT GAA ACA ACA GTC AAC GTT ATC ACT TGT
```

FIG. 7

TATAACGGACGATGAAATGCAATTTA

2506
TGA TTC AAA CAA CAA AAG ATA CAA [TTG] TTC
zzz Phe Lys Gln Gln Lys Ile Gln Leu Phe 2536
AAT TTT [TTG] AAG AGC GGG AGG GAT GAG GGC
Asn Phe Leu Lys Ser Gly Arg Asp Glu Gly 2566
[ATG] TTG AAA CAA CAG TCA ACG TTA TCA CTT
Met Leu Lys Gln Gln Ser Thr Leu Ser Leu 2596
GTG [ATG] ATT GCG ATG TTT GCT GCA TTA ACA
Val Mat Ile Ala Met Phe Ala Ala Leu Thr 2626
GCA GTT GGT GCC TTC ATT AAA ATT CCA TTA
Ala Val Gly Ala Phe Ile Lys Ile Pro Leu 2656
CCG CTC GTG CCG TTT ACA TTA CAA ATT GTC
Pro Leu Val Pro Phe Thr Leu Gln Ile Val 2686
TTT GTC TTT TTA GCG GGT TGC TTA CTC GGT
Phe Val Phe Leu Ala Gly Cys Leu Leu Gly 2716
GGT CGC AAT GGA TTT CAA AGT CAG CTA GTT
Gly Arg Asn Gly Phe Gln Ser Gln Leu Val 2746
TAC ATA GGA ATA GGT TTA GTT GGC TTG CCA
Tyr Ile Gly Ile Gly Leu Val Gly Leu Pro 2776
GTT TTT ACA CAA GGT GGA GGC ATT ACA TAT
Val Phe Thr Gln Gly Gly Gly Ile Thr Tyr 2806
GTA TTG CAG CCG ACT TTT GGT TAC TTA ATA
Val Leu Gln Pro Thr Phe Gly Tyr Leu Ile

FIG. 7 (CONT'D)

```
2836
    GGA TTT GCT CTT GCT GCA TTA GTA ATC GGC
    Gly Phe Ala Leu Ala Ala Leu Val Ile Gly

2866
    TAT ATG ATT GAT CGA GTA GAA TCA CCA ACG
    Tyr Met Ile Asp Arg Val Glu Ser Pro Thr

2896
    AAA AAG CAT TTC ATT GTT GCC AAT ATT ATA
    Lys Lys His Phe Ile Val Ala Asn Ile Ile

2926
    GGG CTT ATC ATT ATT TAT GCA GTC GCA GTA
    Gly Leu Ile Ile Ile Tyr Ala Val Ala Val

2956
    CCT TAT TTA TAT GTA GCA TTA AAT GTA TGG
    Pro Tyr Leu Tyr Val Ala Leu Asn Val Trp

2986
    TTA AAC ATG AAA TCA AGT TGG TCT CAT GTA
    Leu Asn Met Lys Ser Ser Trp Ser His Val

3016
    TTT TTA GTA GGC TTT GTC AAT AGT ATT GTT
    Phe Leu Val Gly Phe Val Asn Ser Ile Val

3046
    GCA GAC TTT TGC TTA GCA ATT GCT TCT GCC
    Ala Asp Phe Cys Leu Ala Ile Ala Ser Ala

3076
    CTT TTA GCT GAA CGT CTA TAC AAA GTA TTC
    Leu Leu Ala Glu Arg Leu Tyr Lys Val Phe

3106
    CGT TCC GCT AGA GCT ATA AAA CTT GTC CAA
    Arg Ser Ala Arg Ala Ile Lys Leu Val Gln 3136                                      3166
ATT GAA AAG GAG AAT GTT TAG TGA ATT GGT TAC AAT
Ile Glu Lys Glu Asn Val zzz zzz

3196
    TAG CAG ATG  AAG TGA TTG CAG GCA AGG TA
```

FIG. 8

TATAAAACTTGTGCAAAT

```
3138      RBS
     TGA AAA GGA GAA TGT TTA GTG  AAT TGG TTA
     zzz Lys Gly Glu Cys Leu Val  Asn Trp Leu 3168
     CAA TTA GCA GAT GAA GTG  ATT GCA GGC AAG
     Gln Leu Ala Asp Glu Val  Ile Ala Gly Lys 3198
     GTA ATT AGC GAT GAT GAG GCA CTT GCC ATT
     Val Ile Ser Asp Asp Glu Ala Leu Ala Ile 3228
     TTA AAT AGT GAT GAT GAT GAT ATT TTA AAG
     Leu Asn Ser Asp Asp Asp Asp Ile Leu Lys 3258
     CTA ATG  GAC GGC GCA TTT GCC ATT CGT AAG
     Leu Met  Asp Gly Ala Phe Ala Ile Arg Lys 3288
     CAC TAT TAC GGT AAA AAA GTA AAG TTA AAT
     His Tyr Tyr Gly Lys Lys Val Lys Leu Asn 3318
     ATG ATT ATG AAT GCT AAA AGT GGC TAT TGC
     Met Ile Met Asn Ala Lys Ser Gly Tyr Cys 3348
     CCA GAG GAT TGT GGC TAT TGC TCG CAG TCA
     Pro Glu Asp Cys Gly Tyr Cys Ser Gln Ser 3378
     TCT AAA TCG ACC GCT CCT ATT GAG AAA TAT
     Ser Lys Ser Thr Ala Pro Ile Glu Lys Tyr 3048
     CCG TTC ATT ACA AAA GAA GAA ATA TTA GCG
     Pro Phe Ile Thr Lys Glu Glu Ile Leu Ala 3438
     GGG GCA AAG CGT GCG TTT GAA AAT AAA ATT
     Gly Ala Lys Arg Ala Phe Glu Asn Lys Ile
```

FIG. 8 (CONT'D)-1

```
3468
    GGT ACG TAT TGC ATC GTC GCA AGC GGA CGT
    Gly Thr Tyr Cys Ile Val Ala Ser Gly Arg

3498
    GGG CCG ACT CGT AAA GAT GTC AAT GTA GTG
    Gly Pro Thr Arg Lys Asp Val Asn Val Val

3528
    AGT GAA GCC GTT GAA GAA ATT AAA GCA AAA
    Ser Glu Ala Val Glu Glu Ile Lys Ala Lys

3558
    TAT GGC TTA AAA GTT TGC GCT TGC TTA GGT
    Tyr Gly Leu Lys Val Cys Ala Cys Leu Gly

3588
    TTA CTA AAA GAA GAA CAA GCA CAA CAA TTA
    Leu Leu Lys Glu Glu Gln Ala Gln Gln Leu

3618
    AAA GAA GCG GGT GTT GAT CGC TAC AAT CAT
    Lys Glu Ala Gly Val Asp Arg Tyr Asn His

3648
    AAC TTA AAT ACA TCA GAG CGT CAC CAT TCC
    Asn Leu Asn Thr Ser Glu Arg His His Ser

3678
    TAT ATT ACG ACG ACG CAC ACA TAT GAG GAT
    Tyr Ile Thr Thr Thr His Thr Tyr Glu Asp

3708
    CGT GTT AAT ACC GTT GAG GTT GTA AAG AAA
    Arg Val Asn Thr Val Glu Val Val Lys Lys

3738
    CAT GGT ATT TCC CCA TGT TCT GGA GCC ATT
    His Gly Ile Ser Pro Cys Ser Gly Ala Ile

3768
    ATT GCG ATG AAA GAA ACG AAA ATG GAT GTC
    Ile Gly Met Lys Glu Thr Lys Met Asp Val

3798
    GTG GAA ATT GCA CGC GCA TTG CAT CAG TTG
    Val Glu Ile Ala Arg Ala Leu His Gln Leu
```

FIG. 8 (CONT'D)-2

3828
```
GAC GCG GAT TCA ATT CCA GTT AAC TTC TTA
Asp Ala Asp Ser Ile Pro Val Asn Phe Leu
```

3858
```
CAT GCA ATT GAT GGA ACG AAA CTT GAA GGA
His Ala Ile Asp Gly Thr Lys Leu Glu Gly
```

3888
```
ACA CAG GAC TTA AAT CCT CGC TAT TGC TTA
Thr Gln Asp Leu Asn Pro Arg Tyr Cys Leu
```

3918
```
AAA GTA TTA GCG TTA TTC CGC TAC ATG AAT
Lys Val Leu Ala Leu Phe Arg Tyr Met Asn
```

3948
```
CCT TCG AAG GAA ATT AGA ATT TCC GGT GGT
Pro Ser Lys Glu Ile Arg Ile Ser Gly Gly
```

3978
```
CGC GAA GTC AAT TTA GGA TTC CTT CAG CCA
Arg Glu Val Asn Leu Gly Phe Leu Gln Pro
```

4008
```
TTT GGA CTG TAT GCA GCA AAT AGT ATT TTT
Phe Gly Leu Tyr Ala Ala Asn Ser Ile Phe
```

4038
```
GTT GGG GAT TAC TTA ACT ACT GAA GGA CAA
Val Gly Asp Tyr Leu Thr Thr Glu Gly Gln
```

FIG. 8 (CONT'D)-3

4068
```
GAA GCC AAT AGC GAT TAT CGT ATG CTT GAA
Glu Ala Asn Ser Asp Tyr Arg Met Leu Glu
```

4098
```
GAT TTG GGC TTT GAA ATC GAG CTG ACA CAA
Asp Leu Gly Phe Glu Ile Glu Leu Thyr Gln
```

4128
```
AAG CAA GAA GAA GCA TTT TGT TCT TAA TTC
Lys Gln Glu Glu Ala Phe Cys Ser zzz
```

4158
```
AAC CAA TCA TTA TGA AAT AAA ATC TAC TAC
```

4188
```
TAC ACA ATA TGA TTA CCT CAA AAC CGT GTG
```

4218                                          4248
```
AGCGTCGTGGAAAAGGCGCACAGACGGTTTTTTGGTCGA
```

4278
```
TAAAAGAGAAGGAGAAAGGTAAATAAATGGTTCCGATAATA
```

4308
```
TACCTATAAAATGATGGTTTTCACAAATGTTCAATGAAA
```

4388
```
    GCGTTTTGAAATTGAACAGTTTGTGAAGGGCTTCACATAAAGC
```

AAACAATTTAATCTACCTTCCTATCTATAAATGTGTTAACTTAATTATTATTAAGGTTAACTCAAATTGAAGAAGTTAG

1131
AAT GGG AGG AAT AGG AGG ATG CGA AAG TTT TCT ACA TAT GAT CTT GCT
Asn Gly Arg Asn Arg Arg Met Arg Lys Phe Ser Thr Tyr Asp Leu Ala

1161

CAG ATT TCA TTA CTA GCT TGT CTT ATT ATC GTT ACA GGC ATG
Gln Ile Ser Leu Leu Ala Cys Leu Ile Ile Ile Val Thr Gly Met

1191

TTT AAG ATT CCA ACA GGT ATT CCT GGA TCT GAG TTT CAA TTA TCA GCA
Phe Lys Ile Pro Thr Gly Ile Pro Gly Ser Glu Phe Gln Leu Ser Ala

1221

CCG ATT GCC GTT GCG ATT GCA GCA GTA TTT GGA TTT AAG CGA
Pro Ile Ala Val Ala Ile Ala Ala Val Phe Gly Phe Lys Arg

1251

1281

FIG. 17A LORF X (CON'T)

```
1311
TAT TTT CTT GCG GGA ATC ATT GCA AGT CTA ATC TTA TTT TTA CTA GGT
Tyr Phe Leu Ala Gly Ile Ile Ala Ser Leu Ile Leu Phe Leu Leu Gly
                                1341

1371
ATA CAC TCC ATC TTA AAT GTT GAA ATT TCA ATA ATT TTC CGA
Ile His Ser Ile Leu Asn Val Glu Ile Ser Ile Ile Phe Arg

1401
TTG ACT GTT GGT CTA ATC ATT GTT TTA GGA ACT TCA ATT CCG GTA
Leu Thr Val Gly Leu Ile Ile Val Leu Leu Gly Thr Ser Ile Pro Val
                                    1431

1461
CTA GTT GTG GCA GGA CCG ATT GGA ACA ATG GTT GCT AGA CTT
Leu Val Val Ala Gly Pro Ile Gly Thr Met Vel Ala Arg Leu
```

FIG. 17B LORF X

```
1491                                    1521
    GGA TTG GCT TTT ACG TTA GGG ACC CCG TTT TTG CCA CTA TTC GTT TTG
    Gly Leu Ala Phe Thr Leu Gly Thr Pro Phe Leu Pro Leu Phe Val Leu

1551
GCG ATT CCA GGG ATG GTC ATT ACG GCT GTC AGT GTT TAT CCA
Ala Ile Pro Gly Met Val Ile Thr Ala Val Ser Val Tyr Pro 1581                                    1611
    ATA ACG AAA ATG TTA TAT GCA ATT AAT AAG AAA GTA GCA GGT GAT CAT
    Ila Thr Lys Met Leu Tyr Ala Ile Asn Lys Lys Val Ala Gly Asp His

1641
CAT GTT AGA AAC GTG TTA TAG CAT TCG AAT GCG TGC AGC TGA
His Val Arg Asn Val Leu ***

1671                      1701                                    1731
    AAAAAATCTCGAAGGAGGAGAAAAGCATAT
```

FIG. 18A LORF W

TTTACGTTAGGGACCCCGTTTTTGCCACTATTCGTTTTGGCGATTCCAGGGATGGTC

ATTACGGCTGTCAGTGTTTATCCAATAACGAAAATGTTATATGCAATTAATAAGAAAGTAG

```
1618                                              1648
    CAG GTG ATC ATC ATG TTA GAA ACG TGT TAT AGC ATT CGA ATG CGT
    Gln Val Ile Ile Met Leu Glu Thr Cys Tyr Ser Ile Arg Met Arg

1678
GCA GCT GAA AAA AAT CTC GAA GGA GGA GAA AAG CAT ATA TCT GGT
Ala Ala Glu Lys Asn Leu Glu Gly Gly Glu Lys His Ile Ser Gly 1708                                          1738
    GGG GAA CGG ATA GGG AGT GAA TTT CAA ATA GAG CCA ATT GTA AAA
    Gly Glu Arg Ile Gly Ser Glu Phe Gln Ile Glu Pro Ile Val Lys

1768
CAG TTA TTG AAC AAA GCA AGG AAT CAT TCG CGC GGA GAT GCT GAC
Gln Leu Leu Asn Lys Ala Arg Asn His Ser Arg Gly Asp Ala Asp 1798                                              1828
    TTT ATT CAA ATT ACC GTT GAA AAA CTT ACA GGT GAT CAG ATA CTG
    Phe Ile Gln Ile Thr Val Glu Lys Leu Thr Gly Asp Gln Ile Leu

1858
TAT ATG CCA CCG TTA GAA ATA ACG ACA ATT GAT GAG AGT TCA ATT
Tyr Met Pro Pro Leu Glu Ile Thr Thr Ile Asp Glu Ser Ser Ile 1888                                              1918
    GAA AGG GCA CAT AAA GAA GCT AGG AGT ATA TTA ACC TCA GTA GGT
    Glu Arg Ala His Lys Glu Ala Arg Ser Ile Leu Thr Ser Val Gly

1948
GTT TCC AAG CAG GCA CAA AAT GTT GCT TTT CAT CTA CTT GCT AGT
Val Ser Lys Gln Ala Gln Asn Val Ala Phe His Leu Leu Ala Ser
```

FIG. 18B LORF W

```
1978                                        2008
   AAT CAA AAT CTT CGT GGG GCT ATC CTC CTT CAT AGT CAA ACT GGC
   Asn Gln Asn Leu Arg Gly Ala Ile Leu Leu His Ser Gln Thr Gly

2038
TTA CGA CTT GAC AAT CGC GGA CTG AAA GGC GTT CGA GTA TCA CGA
Leu Arg Leu Asp Asn Arg Gly Leu Lys Gly Val Arg Val Ser Arg 2068                                     2098
   ATC GAT TGG CAA GAC GCT GAT GTA GGT TAC AAT GAG CGT GTT CGT
   Ile Asp Trp Gln Asp Ala Asp Val Gly Tyr Asn Glu Arg Val Arg

2128
GAA GCG CTA GCT CTG GCA ACG AAA GTG GCA AAT TCT CCG TAT ACC
Glu Ala Leu Ala Leu Ala Thr Lys Val Ala Asn Ser Pro Tyr Thr 2158                                     2188
   ATC GCA GAA TTA TGT TGG TCA GAT GAT CCA GAA TAC GTT ACT GGC
   Ile Ala Glu Leu Cys Trp Ser Asp Asp Pro Glu Tyr Val Thr Gly

2218
TAT GTA AGC AAT CAT GAG ATT GGT TAT GTC AGA ATT ACG CCT TTA
Tyr Val Ser Asn His Glu Ile Gly Tyr Val Arg Ile Thr Pro Leu 2248                                     2278
   AAA AGG GAA GGC TGT GAA AGT GGC GGA CGT ATT TTT TTT GTG TCA
   Lys Arg Glu Gly Cys Glu Ser Gly Gly Arg Ile Phe Phe Val Ser

2308
GAT GAA GTT GAG CTA GAA TCA TAT ATA CAC TAT TTA GAA AGA GAA
Asp Glu Val Glu Leu Glu Ser Tyr Ile His Tyr Leu Glu Arg Glu 2338                                     2368
   CCT ATT CTC ATT AGG GGG CAT TTA AAA TGA ATG ATC GCT TTC GAA
   Pro Ile Leu Ile Arg Gly His Leu Lys ***

2398
GGG AAC TGC AAG TAA TAG AAG AGC AAG GAT TGA CAA GGA AGT TAC 2428                         2458
   GTT
```

FIG. 19A L0RF F

TTTTTTGTGTCAGATGAAGTTGAGCTAGAATCATATACACTATTTAGAAAGAACCTATTCTCATTAG

```
2352
     GGG GCA TTT AAA ATG AAT GAT CGC TTT CGA AGG GAA CTG CAA GTA
     Gly Ala Phe Lys Met Asn Asp Arg Phe Arg Arg Glu Leu Gln Val
                                              2382

ATA GAA GAG CAA GGA TTG ACA AGG AAG TTA CGT TTG TTT TCA ACT
Ile Glu Glu Gln Gly Leu Thr Arg Lys Leu Arg Leu Phe Ser Thr
2412

GGA AAT GAA AGT GAG GTA GTG ATG AAT GGT AAG AAA TTT TTG CTA
Gly Asn Glu Ser Glu Val Val Met Asn Gly Lys Lys Phe Leu Leu
2442                                          2472

TTT TCA TCG AAT AAC TAC TTA GGC CTT GCA ACA GAT AGT CGT TTG
Phe Ser Ser Asn Asn Tyr Leu Gly Leu Ala Thr Asp Ser Arg Leu
2502

AAA AAG AAA GCA ACT GAA ACT AAA GGC ATT AGT AAA TAC GGT ACA GGG GCT
Lys Lys Lys Ala Thr Glu Thr Lys Gly Ile Ser Lys Tyr Gly Thr Gly Ala
2532                                          2562
```

FIG. 19A L0RF F (CON'T)

```
2592
GGC GGT TCT CGA ACA CTT ACA ACT GGA AAC TTC GAC ATT CAT GAA CAG
Gly Gly Ser Arg Thr Leu Thr Thr Gly Asn Phe Asp Ile His Glu Gln 2622                                              2652
    CTA GAA TCT GAA ATT GCA GAT TTT AAA AAG ACT GAA GCG GCC ATT
    Leu Glu Ser Glu Ile Ala Asp Phe Lys Lys Thr Glu Ala Ala Ile

GTA TTC AGC AGT GGG TAT TTA GCG AAC GTA GGT GTG ATT TCG AGC
Val Phe Ser Ser Gly Tyr Leu Ala Asn Val Gly Val Ile Ser Ser 2712                                              2742
    GTG ATG AAG GCA GGA GAT ACT ATC TTT TCT GAT GCT TGG AAT CAC
    Val Met Lys Ala Gly Asp Thr Ile Phe Ser Asp Ala Trp Asn His
```

FIG. 19B LORF F

```
         2772
GCG AGT ATT ATA GAT GGT TGT CGA TTA AGT AAA GCC AAA ACG ATT
Ala Ser Ile Ile Asp Gly Cys Arg Leu Ser Lys Ala Lys Thr Ile 2802                                    2832
    GTT TAT GAA CAT GCG GAT ATG GTG GAT TTA GAG CGG AAA TTA AGG
    Val Tyr Glu His Ala Asp Met Val Asp Leu Glu Arg Lys Leu Arg

2862
CAA TCA CAT GGG GAT GGA TTG AAG TTC ATC GTA ACG GAT GGC GTT
Gln Ser His Gly Asp Gly Leu Lys Phe Ile Val Thr Asp Gly Val 2892                                     2922
    TTT AGT ATG GAT GGT GAT ATT GCG CCA CTT CCA AAA ATA GTA GAG
    Phe Ser Met Asp Gly Asp Ile Ala Pro Leu Pro Lys Ile Val Glu

2952
TTA GCC AAG GAA TAC AAA GCG TAC ATA ATG ATT GAT GAT GCG CAT
Leu Ala Lys Glu Tyr Lys Ala Tyr Ile Met Ile Asp Asp Ala His 2982                                    3012
   GCA ACA GGT GTT CTT GGC AAT GAT GGT TGT GGT ACC GCT GAT TAT
   Ala Thr Gly Val Leu Gly Asn Asp Gly Cys Gly Thr Ala Asp Tyr

3042
TTT GGT TTG AAA GAT GAG ATT GAT TTT ACA GTA GGC ACG TTG AGT
Phe Gly Leu Lys Asp Glu Ile Asp Phe Thr Val Gly Thr Leu Ser 3072                                    3102
   AAA GCG ATT GGT GCA GAG GGT GGA TTT GTA TCG ACA TCA TCC ATT
   Lys Ala Ile Gly Ala Glu Gly Gly Phe Val Ser Thr Ser Ser Ile

3132
GCT AAG AAC TAT TTG TTA AAT AAC GCC CGA TCT TTT ATT TTC CAA
Ala Lys Asn Tyr Leu Leu Asn Asn Ala Arg Ser Phe Ile Phe Gln 3162                                   3192
   ACA GCT TTA TCG CCA AGT GCG ATT GAA GCA GCG CGA GAA GGC ATT
   Thr Ala Leu Ser Pro Ser Ala Ile Glu Ala Ala Arg Glu Gly Ile
```

FIG. 19C LORF F

```
           3222
TCC ATC ATA CAG AAT GAG CCC GAG CGG AGA AAG CAA TTG CTG AAA
Ser Ile Ile Gln Asn Glu Pro Glu Arg Arg Lys Gln Leu Leu Lys 3252                                     3282
    AAT GCG CAG TAC TTA CGA TTG AAA TTA GAG GAA TCT GGT TTT GTA
    Asn Ala Gln Tyr Leu Arg Leu Lys Leu Glu Glu Ser Gly Phe Val

3312
ATG AAA GAA GGG GAA ACA CCT ATT ATT TCT CTT ATC ATT GGT GGT
Met Lys Glu Gly Glu Thr Pro Ile Ile Ser Leu Ile Ile Gly Gly 3342                                       3372
       TCT CAT GAA GCC ATG CAG TTT TCT GCG AAA CTA CTG GAT GAA GGT
       Ser His Glu Ala Met Gln Phe Ser Ala Lys Leu Leu Asp Glu Gly

3402
GTC TTT ATT CCA GCG ATT CGA CCA CCA ACA GTG CCG AAA GGG TCA
Val Phe Ile Pro Ala Ile Arg Pro Pro Thr Val Pro Lys Gly Ser 3432                                       3462
      AGT CGG TTG CGT ATA ACG GTA ATG GCT ACA CAT ACA ATA GAG CAG
      Ser Arg Leu Arg Ile Thr Val Met Ala Thr His Thr Ile Glu Gln

3492
CTC GAT ATG GTC ATT AGT AAA ATT AAG AAA ATA GGA AAA GAA ATG
Leu Asp Met Val Ile Ser Lys Ile Lys Lys Ile Gly Lys Glu Met 3522                                      3552
      GGG ATT GTA TAA TTG TTT GAG TGC CTG GCA CTC AAA CAA TTT TTT
      Gly Ile Val ***

3582
GAT TGC TTT TTC TTA TTA ATT ACA TAG CAC TAA C
```

CLONING OF THE BIOA, BIOD, BIOF, BIOC AND BIOH GENES OF BACILLUS SPRAERICUS, VECTORS AND TRANSFORMED CELLS

The present invention relates to the preparation of biotin by fermentation using the recombinant DNA technique.

Biotin is a vitamin which is necessary for man, animals and plants, and for some microorganisms.

It has been isolated from egg yolk and is found in brewer's yeast, cereals and various organs, in free form or combined with proteins.

This vitamin has been, in particular, proposed as a regulator of cutaneous metabolism, in particular in the treatment of seborrheic dermatitis in man.

Apart from the different sources which have been recalled above, biotin is synthesized by certain microorganisms, especially microorganisms of the genus Bacillus such as *Bacillus sphaericus.*

FIG. 1 shows schematically the chain of biotin biosynthesis from pimelic acid in this type of microorganism. This biosynthetic chain comprises 5 different enzymatic stages in which the genes employed are designated successively bioC, bioF, bioA, bioD and bioB.

The systematic study of the production of biotin from pimelic acid during industrial fermentations has shown that certain microorganisms, especially those belonging to the genus *Bacillus sphaericus,* hyperproduce biotin vitamers as well as biotin (the different intermediates leading to biotin will be referred to hereinafter as "vitamers").

For these bacteria, among biotin precursors, DTB (desthiobiotin) represents the predominant compound which is produced in much larger amounts than the final molecule, namely biotin.

There is a strong control of transcription repressing biotin synthesis which depends on the amount of biotin present in the culture medium; this repression takes place in *E. coli* as well as in *Bacillus sphaericus.*

However, no feedback inhibition regulates biotin biosynthesis in *E. coli* and a control of this kind has never been described in *Bacillus sphaericus.*

The full explanation for the production of a very large amount of DTB (for a small amount of biotin) from pimelic acid in *Bacillus sphaericus* still requires a very substantial molecular biological study to be carried out on the organization and regulation of the pathway of biotin biosynthesis in this bacterium.

Preliminary studies of some of the extracted and semi-purified biosynthetic enzymes from strains of *B. sphaericus* producing DTB do not reveal significant differences from the biotin enzymes that are well known in *E. coli.*

Nevertheless, the production of biotin by industrial fermentation of such strains of *Bacillus sphaericus* (IFO 3525, NCIB 9370) could become competitive with the existing chemical processes if the yield of biotin was improved. In order to achieve this object, it would be advantageous to obtain a constitutive hyperexpression of all the biosynthetic genes for biotin in these strains.

The selection of derepressed strains of *E. coli,* either by their resistance to biotin analogs such as alphadehydrobiotin or by the selection of mutants that hypersecrete biotin, has of course been described. "Cis-dominant" mutations which act pleiotropically on the synthesis of all the biotin genes organized into a bipolar operon have also been described. Trans-acting mutations have also been mentioned although, in addition to their ability to abolish the control of the transcription of the biotin genes, they frequently have pleiotropic properties which may affect the general physiology of the cell.

These methods of traditional microbiological selection may also be applied to the strains of *Bacillus sphaericus* producing DTB if the assumption is made that the molecular control of biotin biosynthesis and the general organization of the biotin genes are the same as in *E. coli.*

Over and above all these assumptions, the use of mutant strains in large-scale industrial fermentations and in continuous culture requires the selection of mutants that show a very low level of reversion, and this represents a difficult task given the absence at present of methods of fine genetic analysis in *Bacillus sphaericus.*

Another approach could consist in cloning all the genes involved in the chain of biotin biosynthesis from a strain of *Bacillus sphaericus* producing DTB, and then in modifying in vitro the 5′ control region so as to abolish the control of transcription.

In addition, the cloning and manipulation of these genes in vitro would enable their general organization to be studied and their in vivo transcription to be improved, using genetic engineering techniques which are known, involving especially the use of strong promoters which are known to be functional in strains of *Bacillus sphaericus.*

The reintroduction of all these hyperexpressed genes which would no longer be regulated by biotin (but which would be regulated in an inducible manner using, for example, induction by an increase in temperature or by a low-cost substrate) into the original strain of *Bacillus sphaericus* could then be carried out using the known techniques of transformation, transduction or conjugation-mobilization.

It is also possible to envisage the introduction of these genes into different microorganisms which are known to be acceptable in the foodstuffs industry and which are permeable to pimelic acid, for example *Bacillus subtilis, Saccharomyces cerevisiae* or strains of Pseudomonas.

Finally, the stabilization of this genetic information in the microorganisms could be achieved by a directed integration in the chromosomes or by a self-selection of plasmids as described, for example, in French Patent No. 84/12,598.

The cloning and characterization of the bioB gene of *Bacillus sphaericus* have already been described in Japanese Patents A-166,992/85 of 29th July 1985, A-66,532/86 of 25th Mar. 1986 and A-95,724/86 of 24th Apr. 1986.

More especially, the present invention relates to the DNA sequences coding for the enzyme produced by one of the following genes involved in the chain of biotin biosynthesis in bacteria:

bioA gene
bioD gene
bioF gene
bioC gene
bioH gene.

Some these DNA sequences according to the invention are linked in the form of a cluster with the bioB gene which had previously been identified, and the whole group hence covers most of the chain of biotin biosynthesis.

Among the DNA sequences of interest, the DNA sequences which code for the enzymes produced by the following genes should be mentioned:

bioB and bioD bioB, bioD and bioA bioB, bioD, bioA and bioF.

This type of sequence used in suitable vectors enables biotin to be prepared from its different vitamers.

The latter can, as will be described below, also be prepared by fermentation using vectors which express the DNA sequences which code for the enzyme or enzymes produced by the following genes:

bioF and bioC bioF and bioH bioF, bioC and bioH, as well as the sequences which code, in addition to the above sequences, for the products of the following genes:

bioA bioA and bioD, or bioA, bioB and bioD.

Although the abovementioned DNA sequences may be of various origins, it is preferable to use the sequences originating from a strain of Bacillus, especially a strain of *Bacillus sphaericus*.

As stated above, it is especially advantageous that these DNA sequences should be devoid of the natural sequences providing for the control of the transcription of the enzymes involved in the pathway of biotin biosynthesis in the original bacterium, in order to abolish the natural regulation due to biotin and to place these DNA sequences under the control of chosen elements which will provide for their efficient transcription in the host strain.

The invention relates, in particular, to all or part of the sequences which are shown in FIGS. 4 to 8 and 17 to 19 and which code for one of the genes mentioned above.

The DNA sequences according to the present invention may be used in different ways.

Preferably, the DNA sequences in question will be carried by a plasmid vector capable of providing for the transformation of a bacterium and containing all the elements providing for the expression of the corresponding genes.

This plasmid may, as has been stated, be of the autonomous and self-replicating type or alternatively, on the other hand, it may be arranged so as to provide for its integration in the chromosome of the host strain.

For this purpose, the different techniques to be employed are known or will be described in the examples.

Thus, in the case of an integration vector, the latter should contain at least one sequence homologous with a sequence present in the genome of the strain to be transformed. thereby enabling chromosomal integration to be ensured. Either a homologous sequence corresponding to a natural genomic sequence or a homologous sequence introduced by another plasmid integration vector may obviously be used.

When the vector is of the autonomous and self-replicating type, it will contain an origin of replication that is effective in the host cell.

Similarly, these different plasmid vectors may contain elements providing for selection, such as a gene for resistance to an antibiotic and/or a marker gene, under the control of a promoter of the strain to be transformed.

Among cells which may be used as a host strain, there should be mentioned, more especially, bacteria, in particular of the genera Escherichia, Bacillus and Pseudomonas, as well as yeasts, especially yeasts of the genus Saccharomyces.

Among host cells that are especially advantageous, *Bacillus sphaericus*, *Bacillus subtilis* and *Excherichia coli* should be mentioned.

Finally, the most especially advantageous strains for transformation by the DNA sequences according to the present invention are the strains which have already been transformed by vectors providing for the expression of other genes involved in this biosynthetic pathway, that is to say the F, A, D and B genes as described in the present application.

Under these conditions, the introduction of the bioC and bioH genes into the bacterium enables this bacterium to synthesize biotin from the first vitamer of the chain, namely pimelate, and this offers considerable economic advantage at the industrial level.

In the context of the present invention, the plasmid integration vector is more especially plasmid pTG475, which will be described below and which contains, in particular, an inducible promoter.

When the vector contains an autonomous origin of replication, the DNA sequences coding for the enzymes mentioned above will preferably be flanked by control elements providing for their expression in the host strain; these will comprise, in particular, at the 5' end, a strong promoter that is effective in the said strain and, where appropriate, other elements such as a termination sequence when the host strain is a yeast or any other microorganism in which such a sequence is necessary.

The present invention also relates to the cells transformed by the vector plasmids according to the invention. Among these cells, there should be mentioned, more especially, bacteria, in particular of the genera Bacillus, Escherichia or Pseudomonas, but also yeasts, especially of the genus Saccharomyces.

Among the strains which may be transformed by these vectors, strains which already produce biotin or one of its vitamers should be mentioned.

Finally, the present invention relates to a method for preparing biotin, wherein a growth medium containing at least pimelic acid, or one of the vitamers of biotin, is fermented with cells as described above which are permeable either to pimelic acid or to the said vitamers of biotin, and wherein the biotin produced is recovered.

The method according to the invention can be carried out in the form of different variants.

In particular, it is possible to prepare the vitamer in situ using cells transformed with a vector according to the invention; in particular a transformed strain containing the bioF, bioH and bioC genes may be capable of producing KAPA from pimelic acid, the conversion of this KAPA to biotin being accomplished by a strain carrying the complementary genes D, A, B for example.

It is possible to arrange for two successive fermentations, or alternatively a co-fermentation if the strains are mutually suited thereto.

It is also possible to arrange for the complementation of a strain which possesses only part of the genes in question, or alternatively to transform a strain which already produces biotin so as to make it overproductive.

Other characteristics and advantages of the present invention will emerge on reading the examples described below with reference to the figures, wherein:

FIG. 3 shows schematically plasmid pTG475,

FIG. 4 shows the non-coding sequence upstream from the No. 1 LORF sequence,

Figure 1:
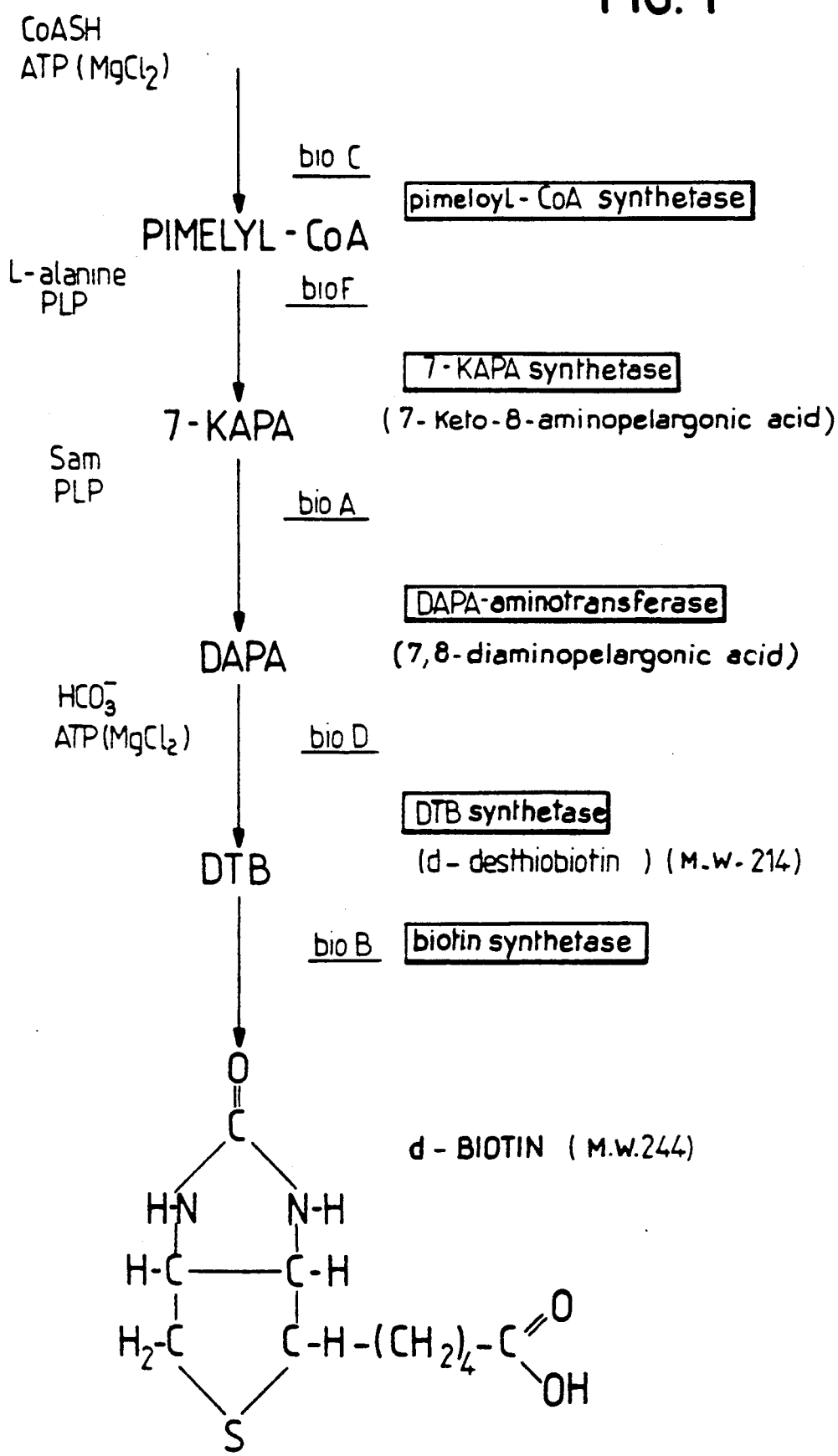
FIG. 1 shows the chain of biotin biosynthesis.
Figure 2:
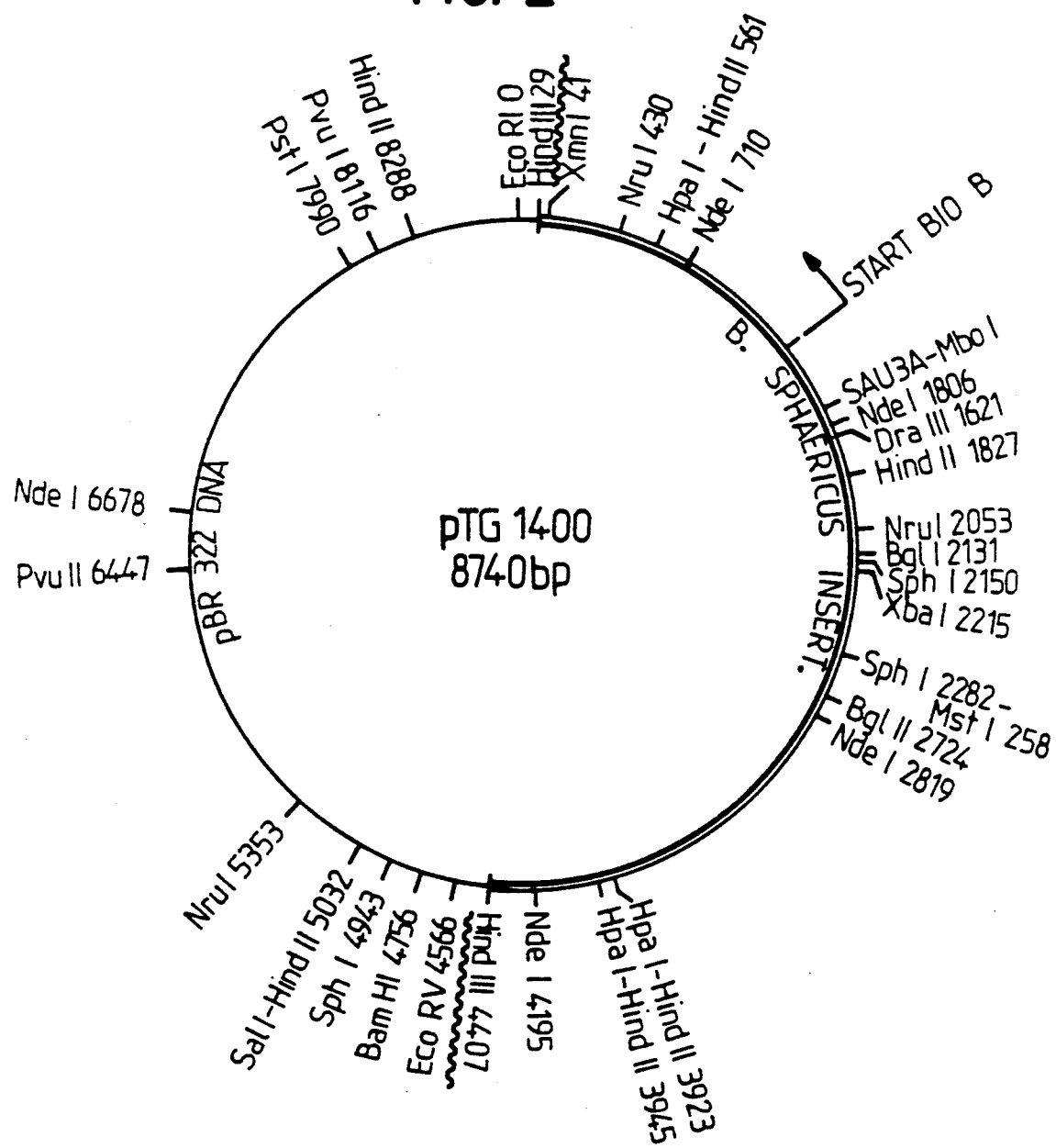
FIG. 2 shows schematically plasmid pTG1400.
Figure 9:
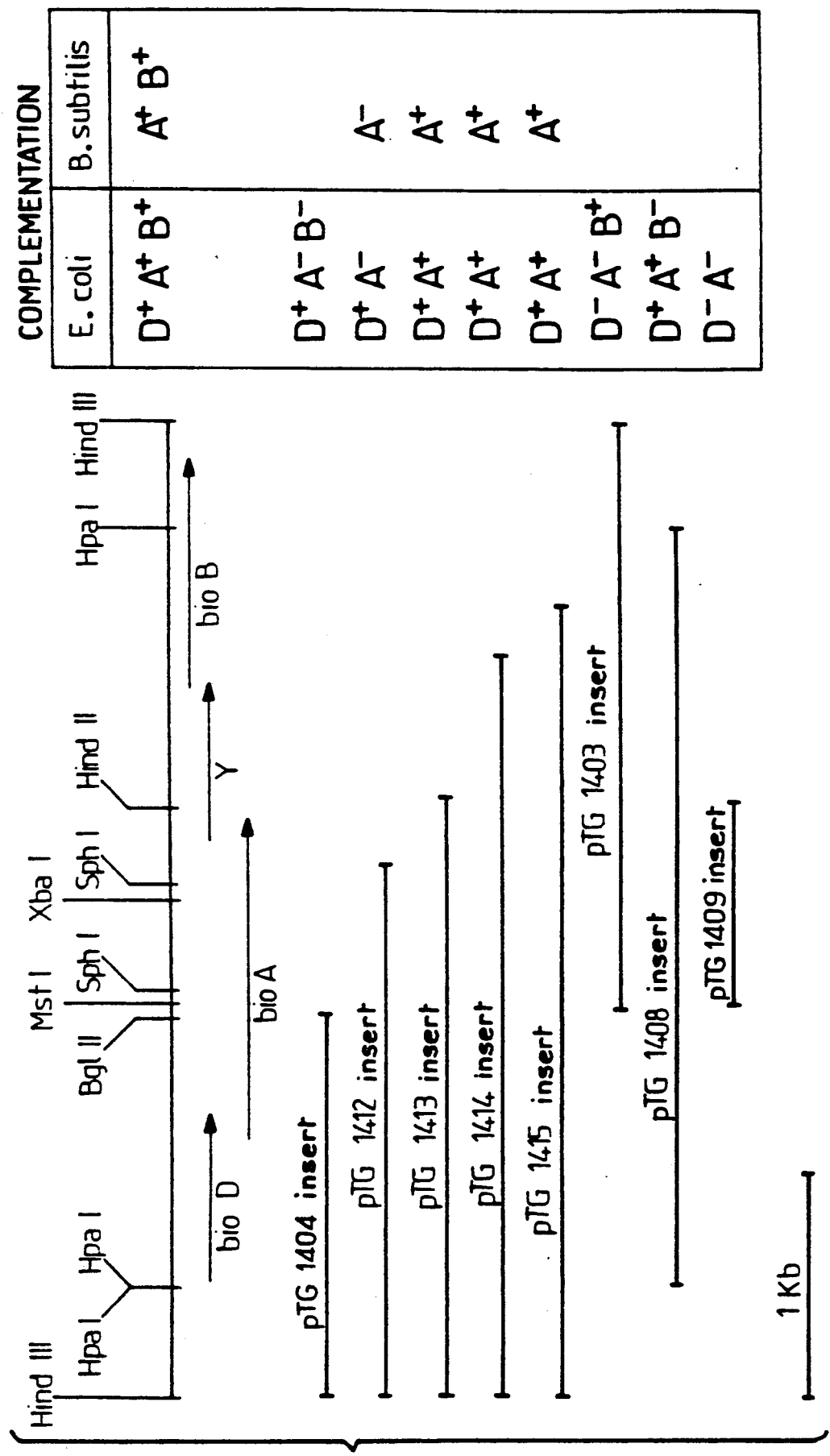
Figure 10:
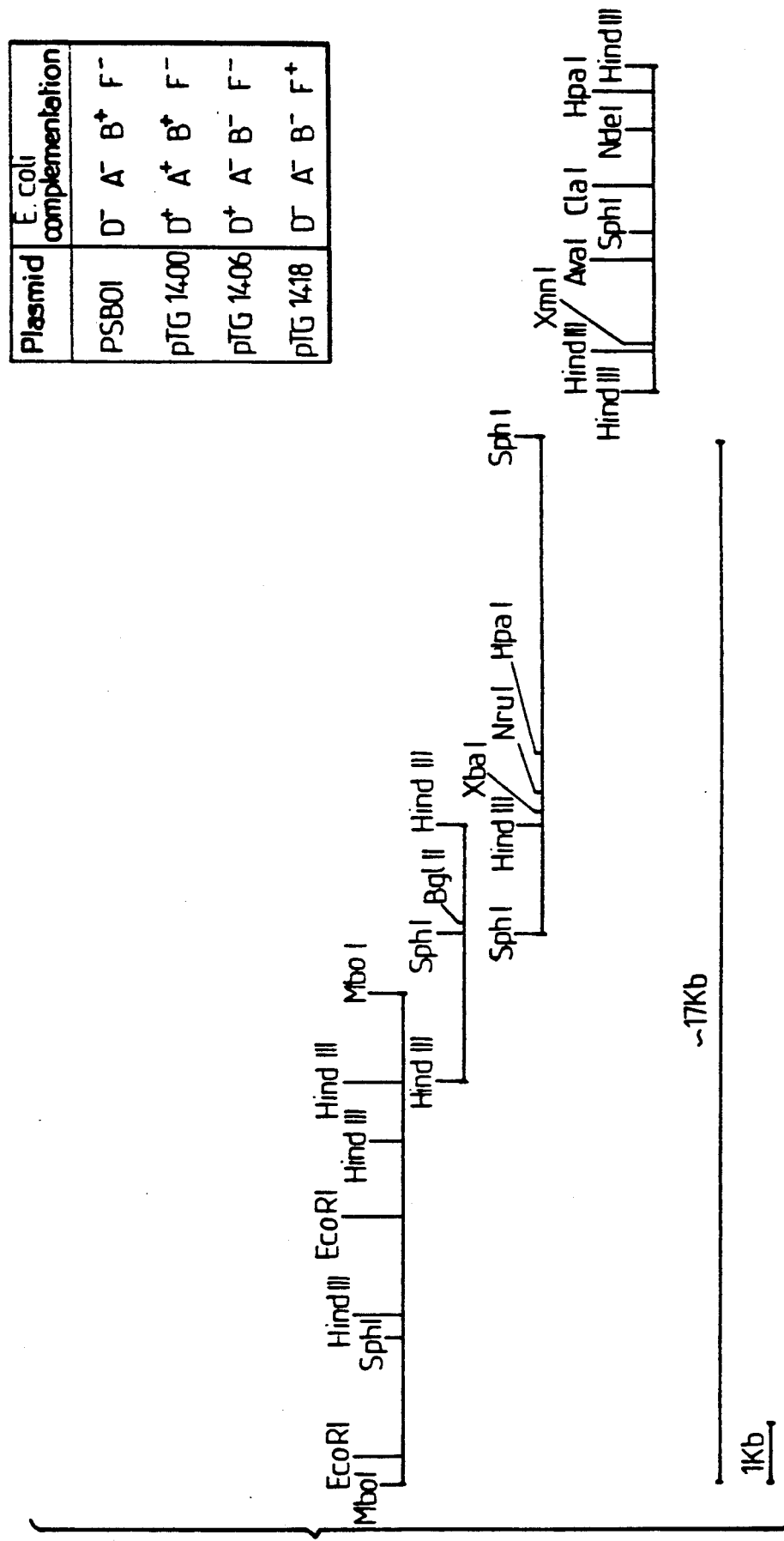
Figure 11:
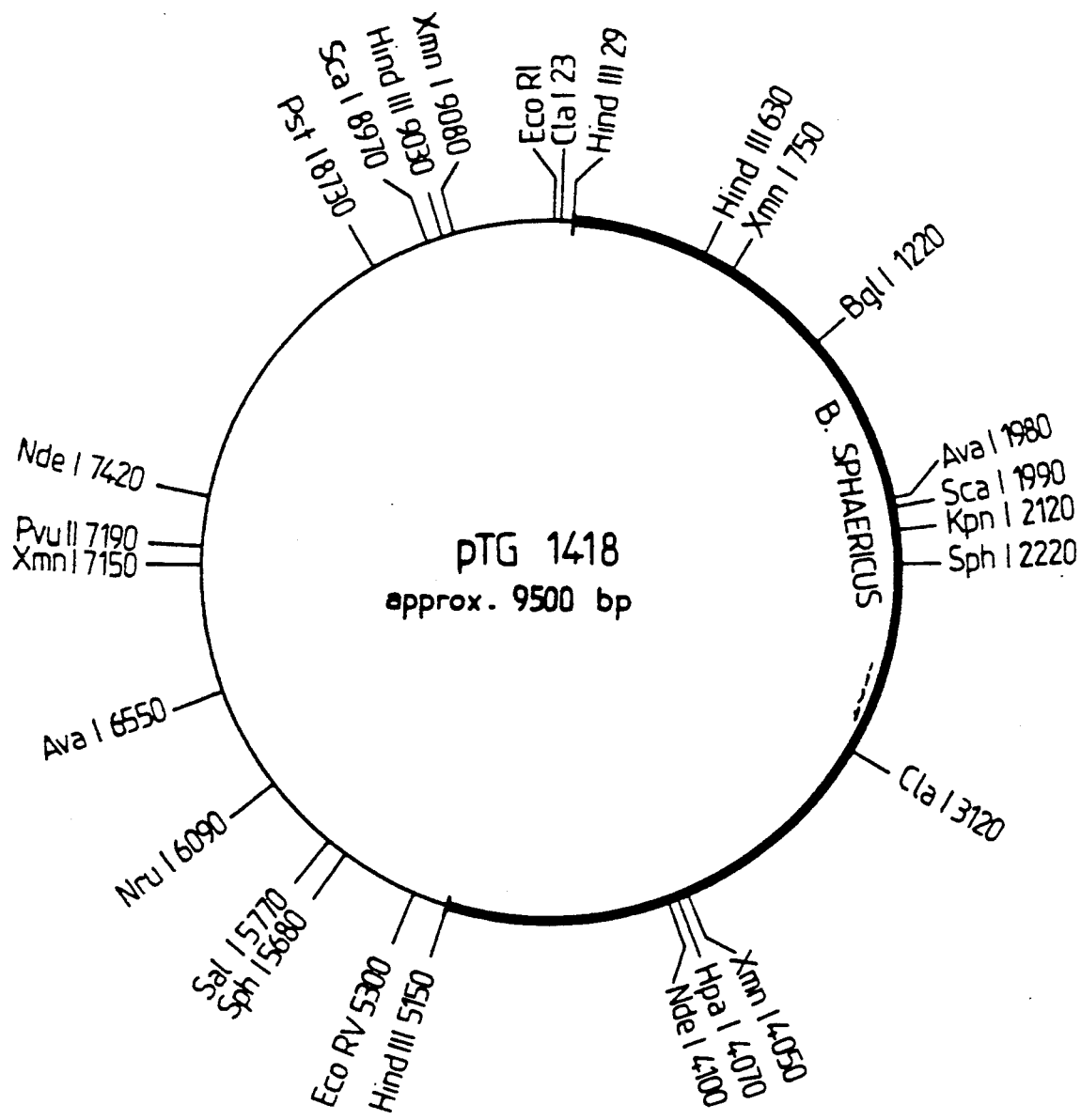
Figure 12:
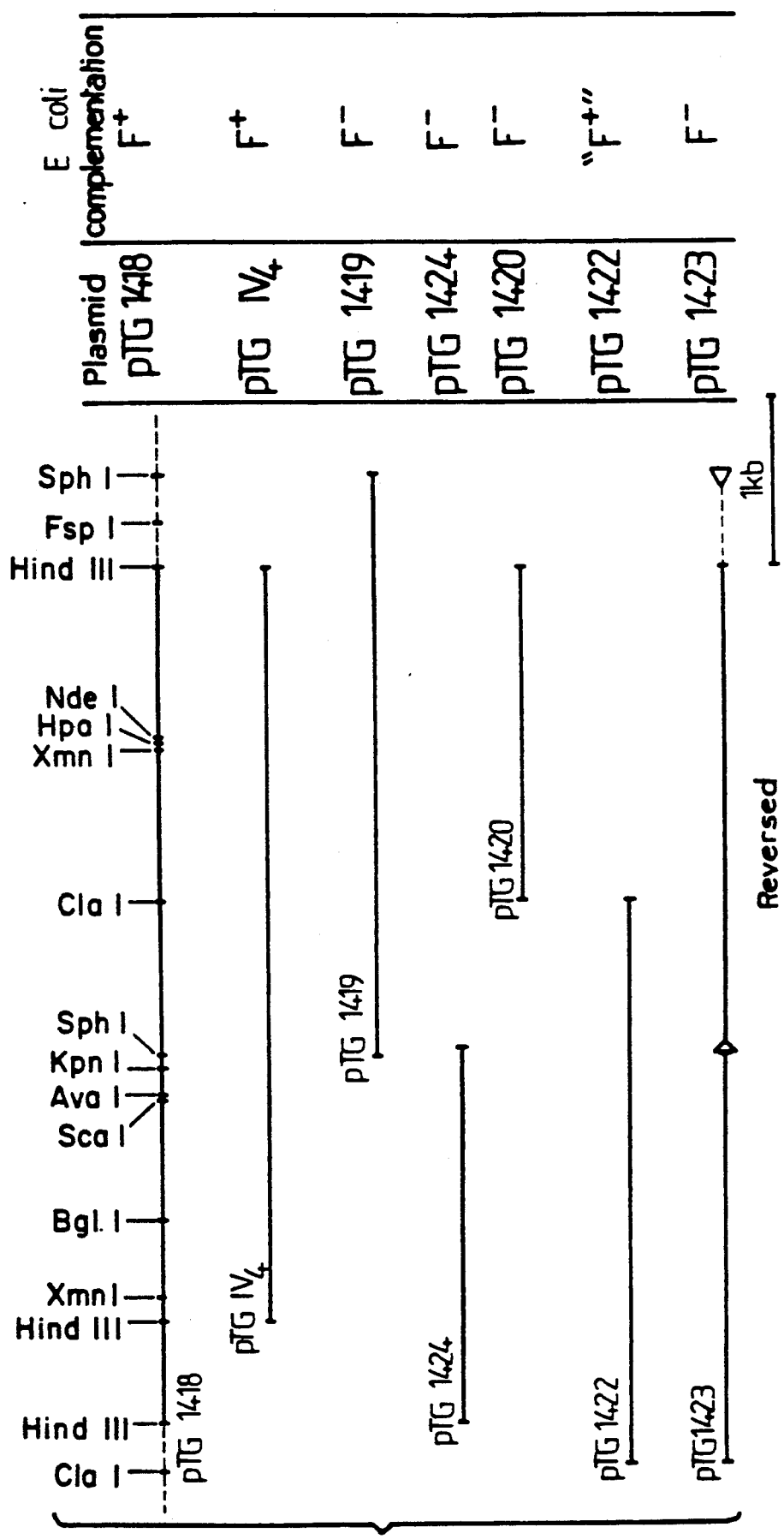
Figure 13:
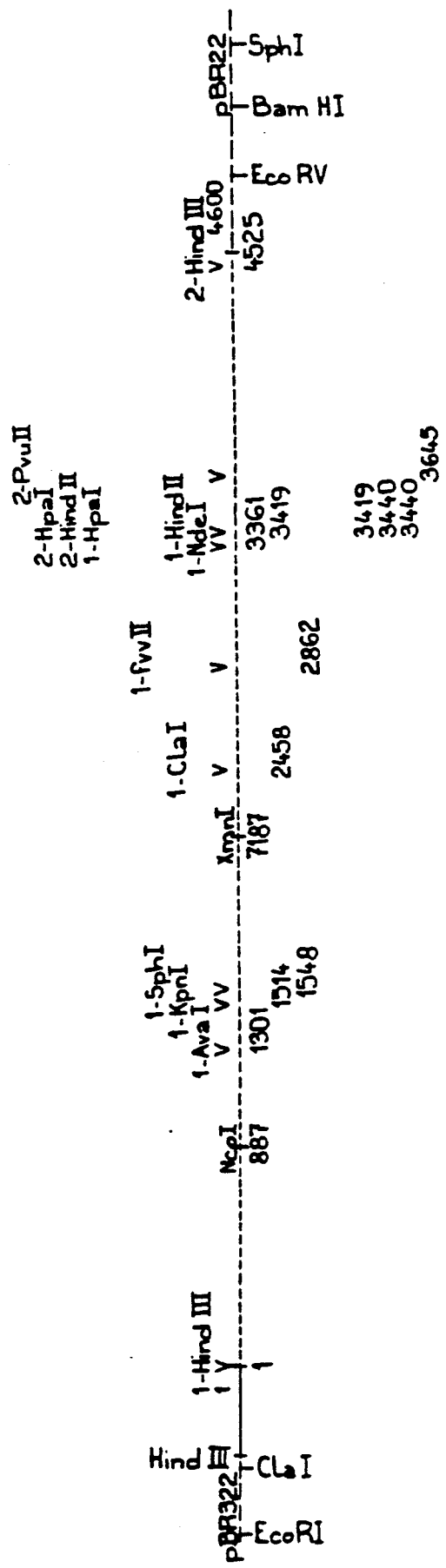
Figure 14A:
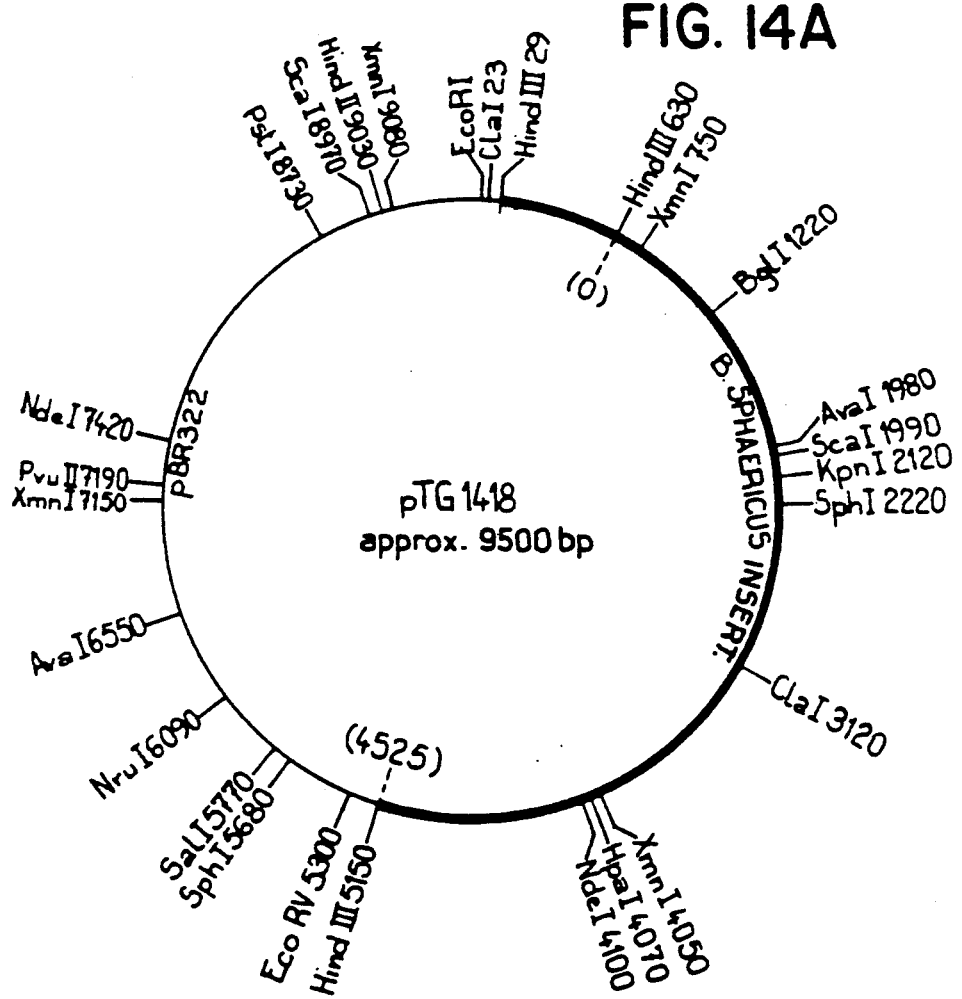
Figure 14B:
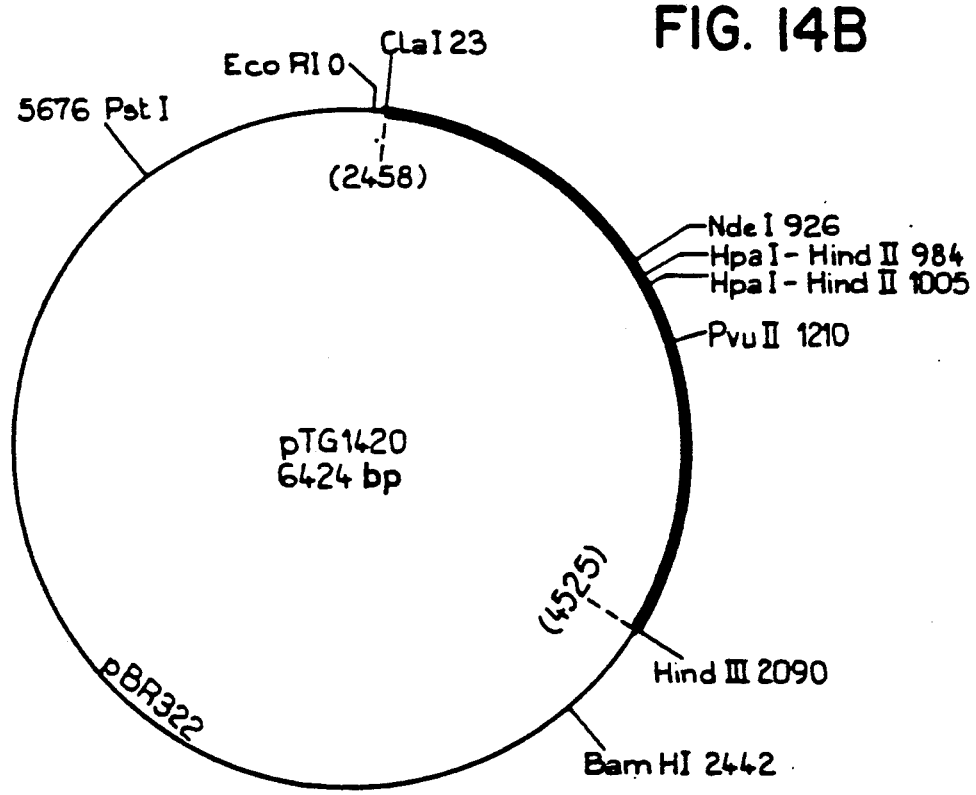
Figure 15A:
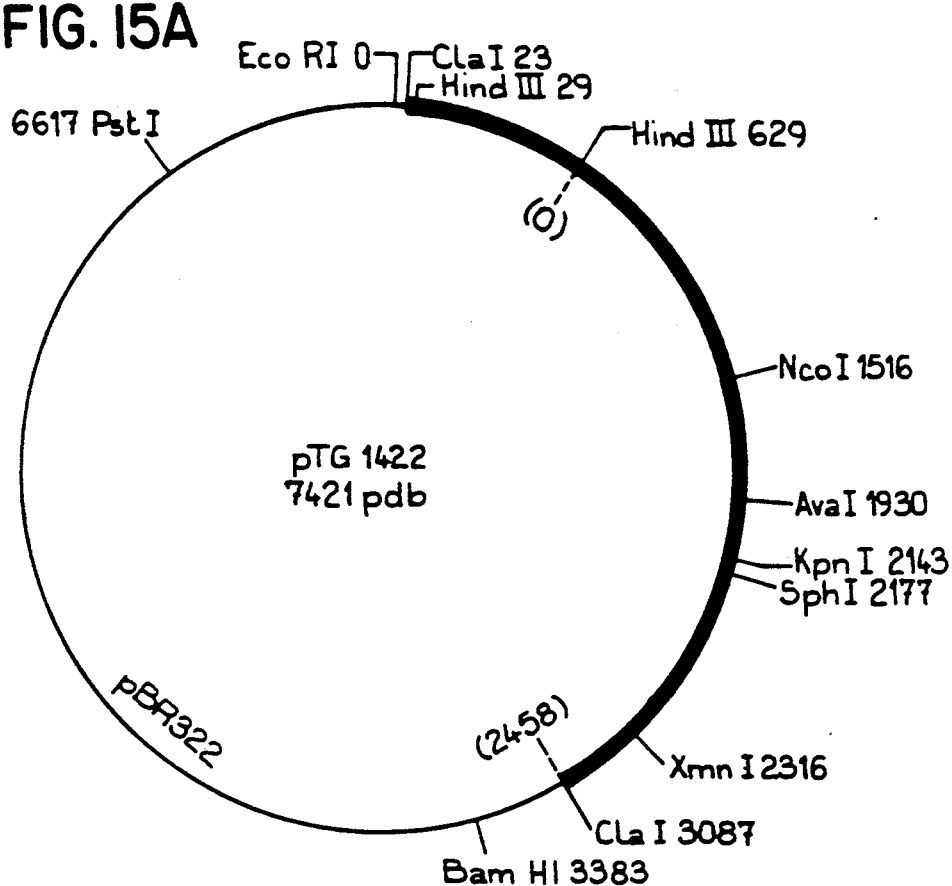
Figure 15B:
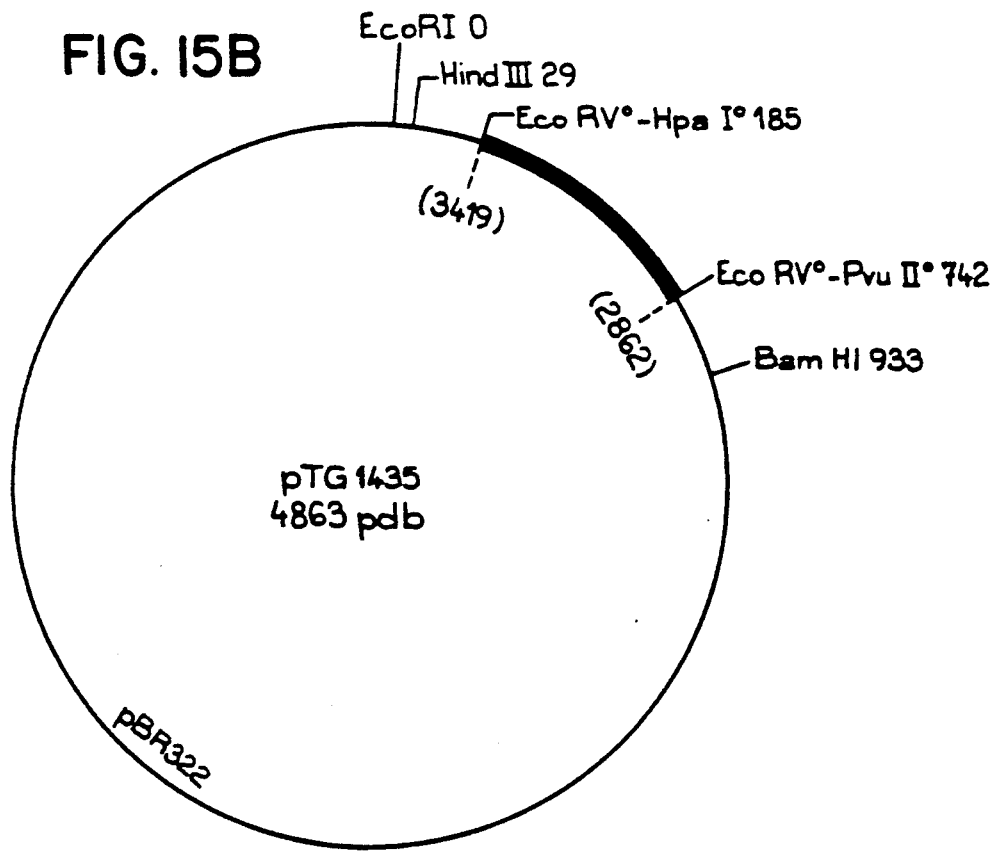
Figure 16A:
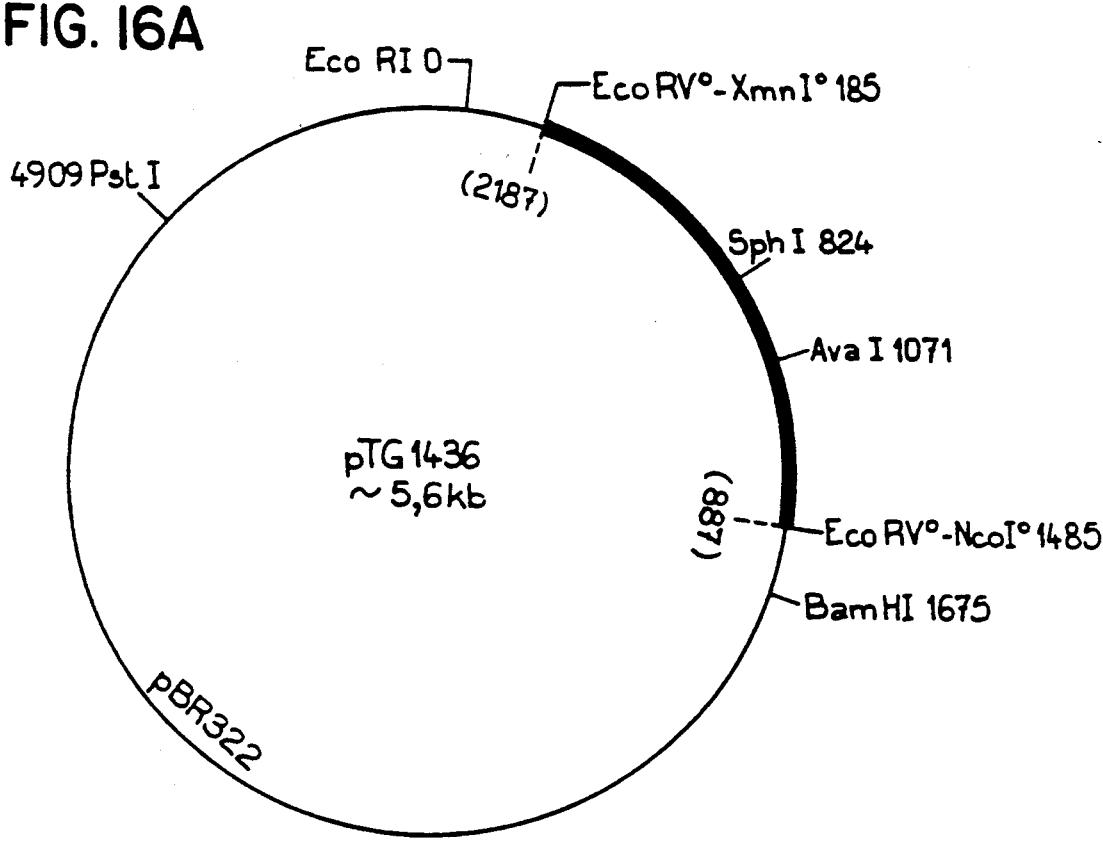
Figure 16B:
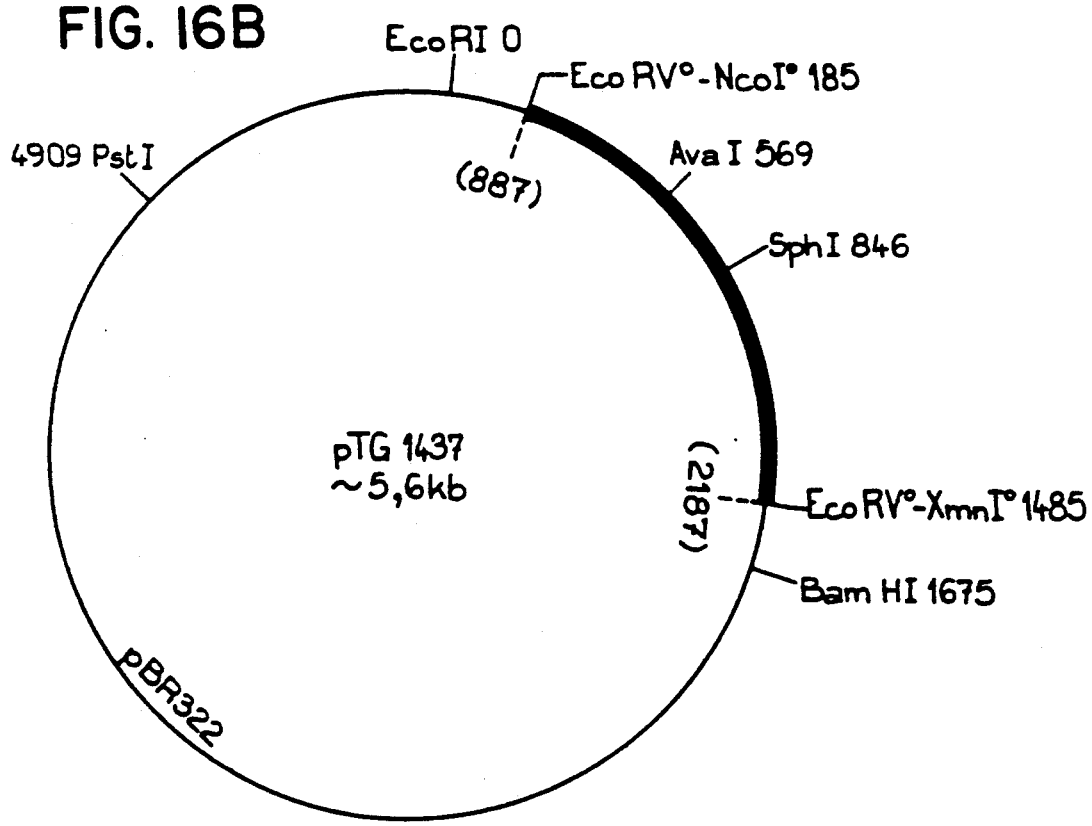
Figure 20:
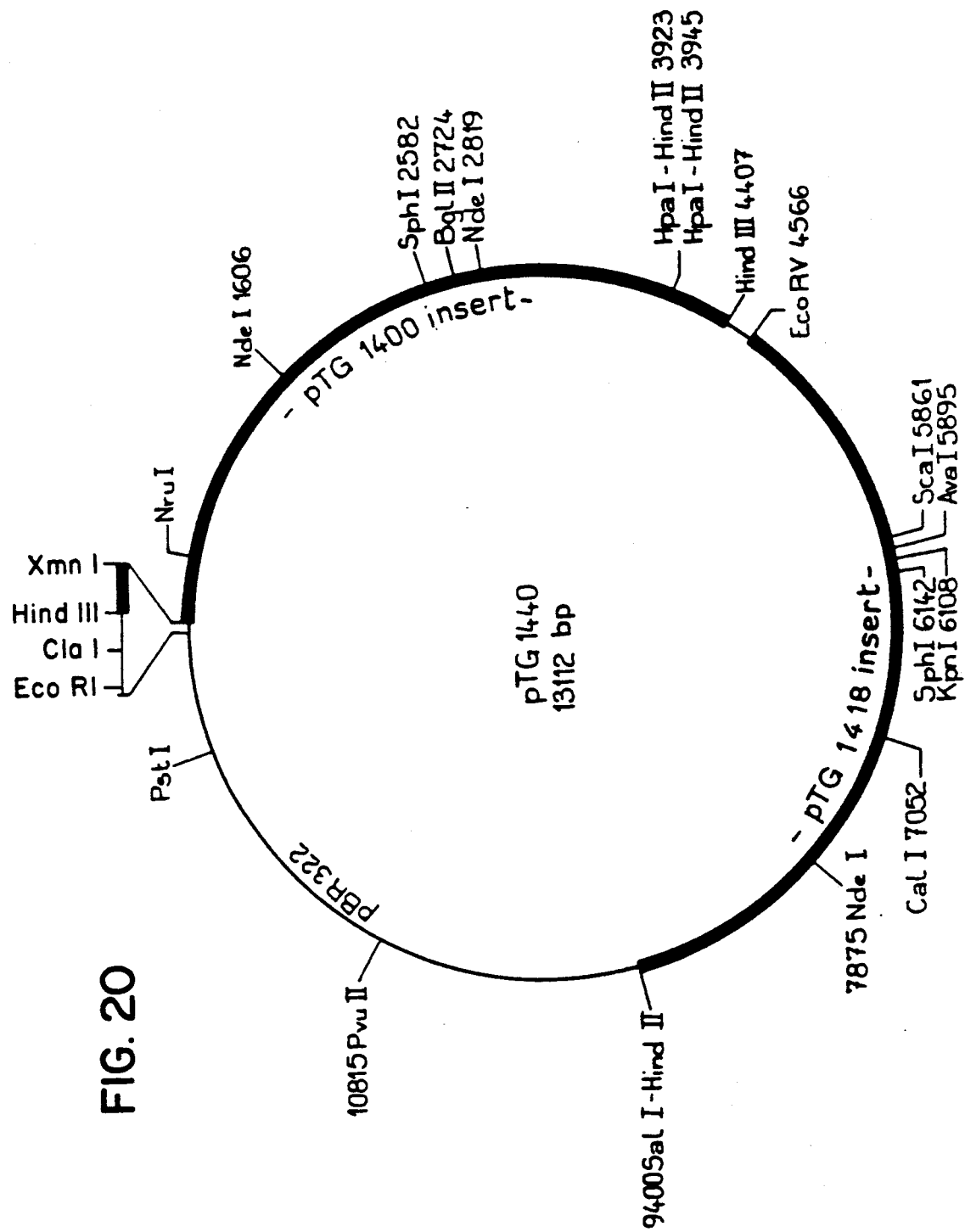
Figure 21:
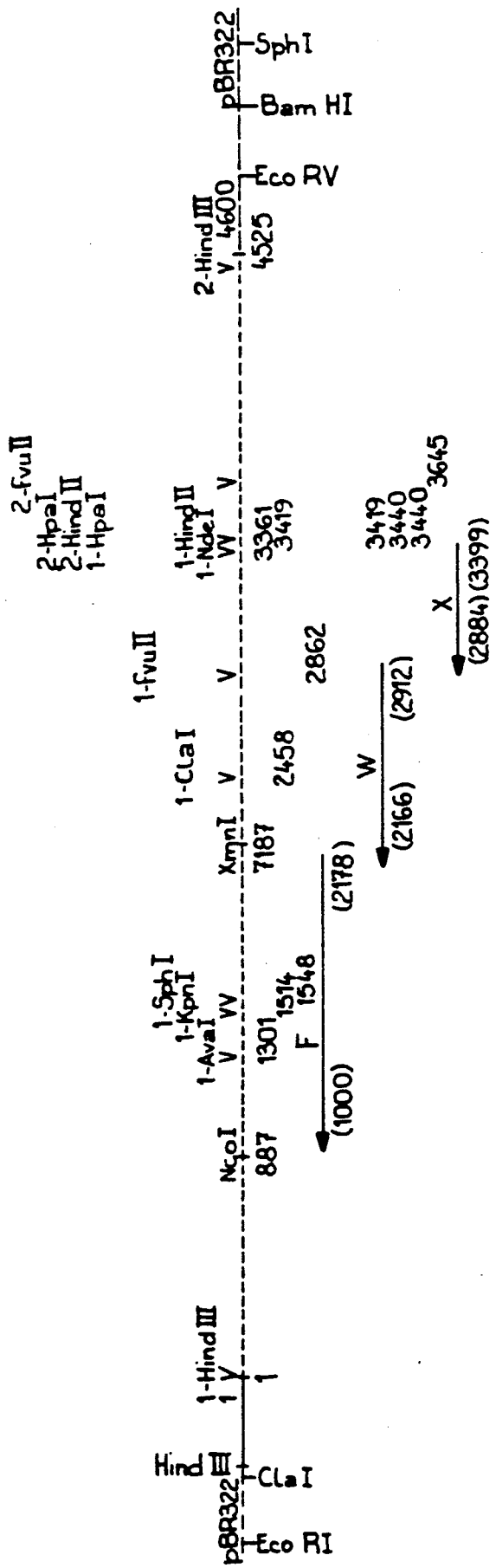
Figure 22:
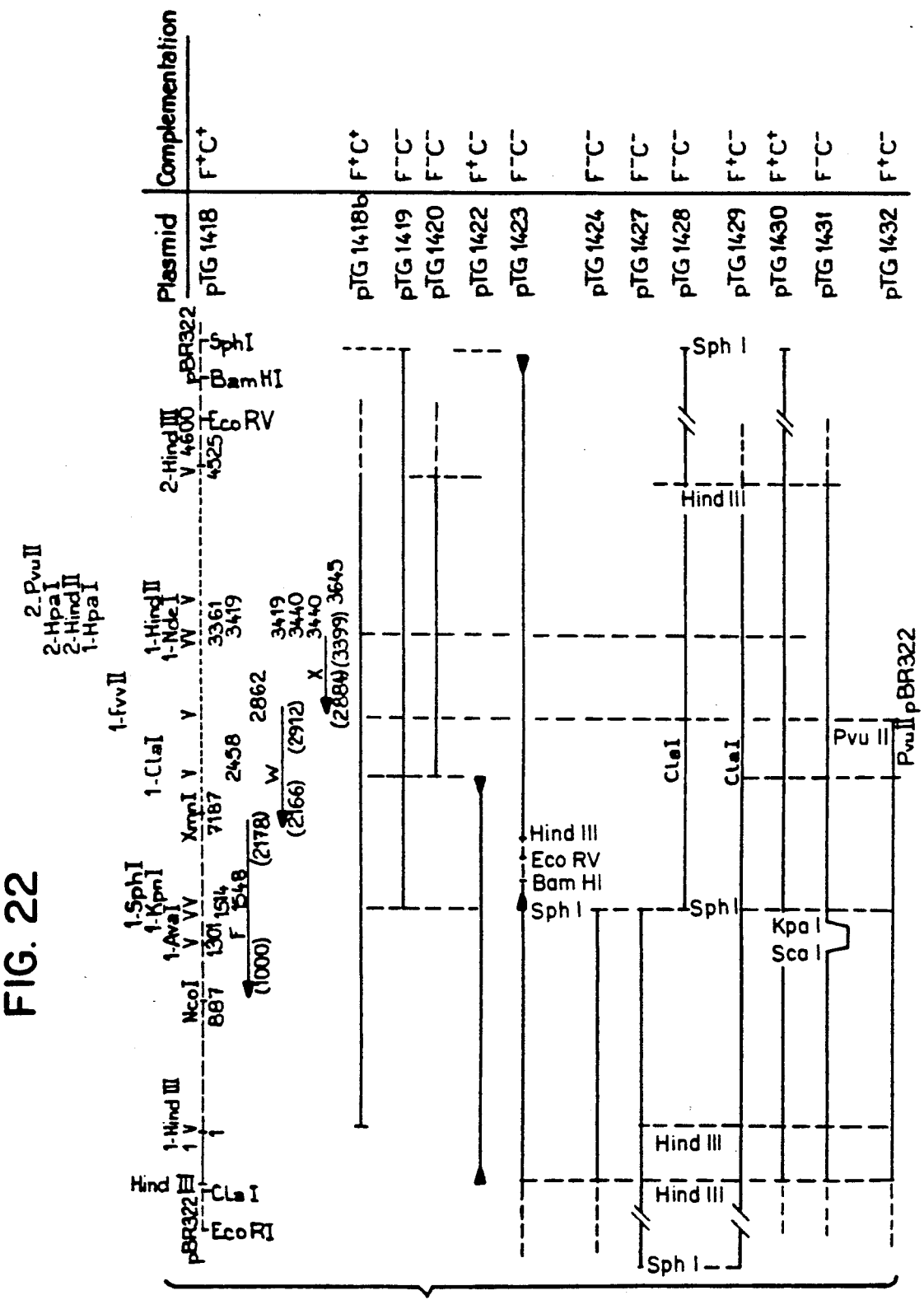
Figure 23:
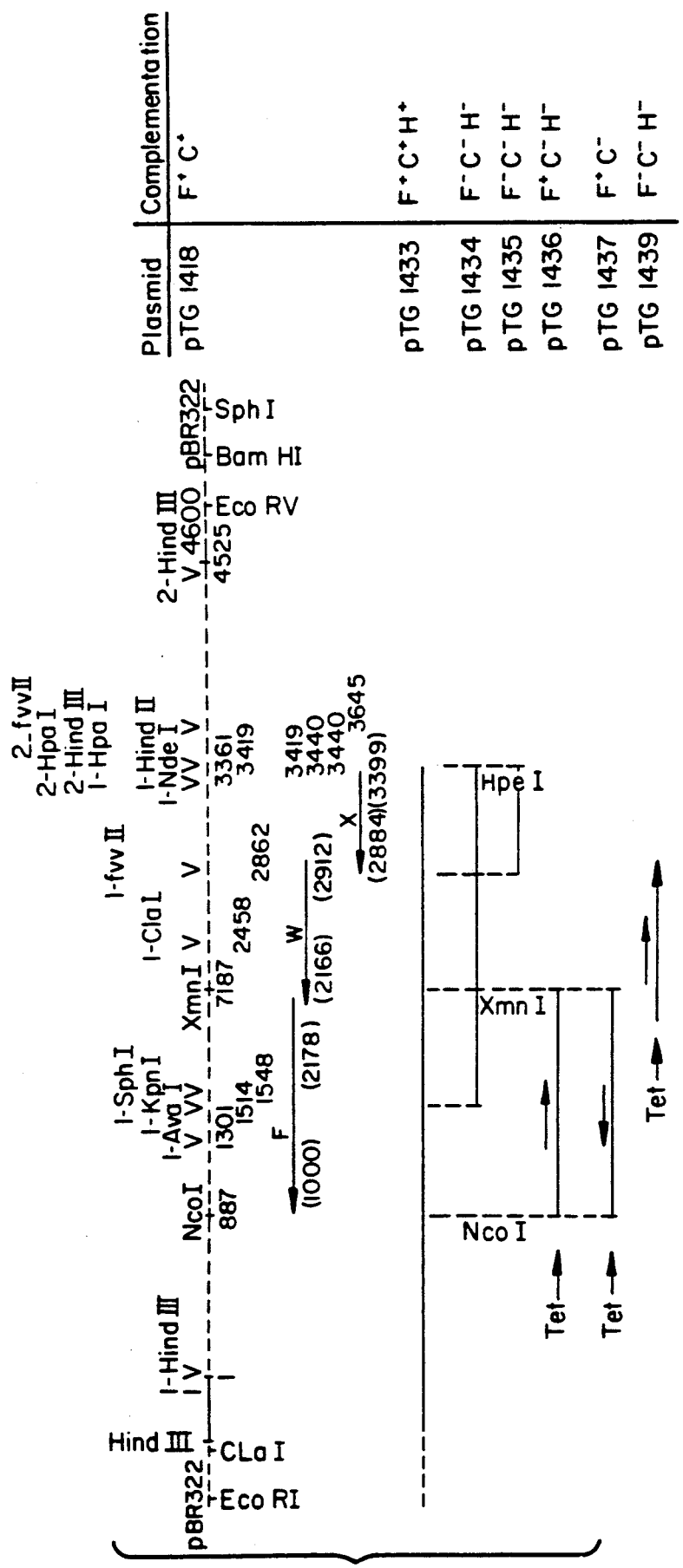

FIGS. 5, 5-1 and 5-2 show the No. 1 LORF sequence corresponding to the bioD gene, FIGS. 6, 6-1, 6-2, and 6-3 show the No. 2 LORF sequence corresponding to the bioA gene, FIGS. 7 and 7(cont'd) show the No. 3 LORF sequence corresponding to the Y gene, FIGS. 8, 8-1, 8-2 and 8-3 show the No. 4 LORF sequence corresponding to the bioB gene, FIG. 9 show schematically the study of complementation of pTG1400, FIG. 10 shows schematically the study of complementation between different plasmids, FIG. 11 shows schematically the structure of plasmid pTG1418, FIG. 12 shows schematically the test of complementation of pTG1418, FIG. 13 shows the restriction map of the insert of *B. sphaericus* used in the following plasmids:

FIGS. 14A and B show schematically plasmids pTG1418 and pTG1420,

FIGS. 15A and B show schematically plasmids pTG1422 and pTG1435,

FIGS. 16A and B show schematically plasmids pTG1436 and pTG1437,

FIGS. 17A, 17A(cont'd), and 17B show the LORF X sequence,

FIGS. 18A and 18B show the LORF W sequence,

FIGS. 19A, 19A(cont'd), 19B, and 19C show the LORF F sequence,

FIG. 20 shows schematically plasmid pTG1440,

FIG. 21 shows the restriction map of the insert of plasmid pTG1418,

FIGS. 22 and 23 show the different plasmids derived from pTG1418 that are used in the complementation tests.

For reasons of simplification, the DNA sequences and the structures of the plasmids have been shown in the attached drawings; it is nevertheless understood that they are to be considered as forming an integral part of the present description.

EXAMPLE 1

Cloning of the bioA and BioD genes of *Bacillus sphaericus* IFO 3525 by complementation and demonstration of their linkage with bioB a) In *E. coli*

*Bacillus sphaericus* IFO 3525 is cultured in 200 ml of PAB culture medium (DIFCO Bacto antibiotic medium 3, 17.5 g/l) at 37° C. for 17 hours. The bacteria are recovered by centrifugation and the whole DNA is then extracted from the cells by Saito's method (Saito et al. BBA 1963, 72, 619–629). A quantity of 450 μg of pure DNA is obtained.

20 μg of the whole DNA is completely restricted with HindIII (3 U/μg of DNA). pBR322 is treated with alkaline phosphatase after being completely digested with HindIII.

The hybrid recombinant plasmids are obtained by mixing the genomic DNA, digested with HindIII (2 μg), and pBR322, treated as above (1 μg), with 2 units of T4 ligase (Boehringer Mannheim) in 50 μl of reaction buffer containing 30 mM NaCl, 30 mM Tris-HCl pH 7.5, 10mM MgCl$_2$, 0.2 mM EDTA pH 8, 2 mM DTT, 0.5 mM ATP pH 7 and BSA 0.1 mg/ml. The incubation is performed at 14° C. for 16 hours. Aliquots of the ligation mixture are then added in a transformation experiment [Cohen et al. (1972) PNAS 69, 2110–2114], using *E. coli* strain C600 r$_K$−m$_K$+ and selecting the strains for their resistance to ampicillin (100 μg/ml) on LB medium.

4 different pools of plasmid DNA are then extracted, each corresponding to an average of $10^4$ individual clones on the transformation dishes.

Different bio mutants of *E. coli* are then transformed with these DNA pools and the transformants are selected either in the presence of ampicillin (100 μg/ml) on LB medium or for resistance to this antibiotic, and for prototrophy for biotin at the same time (LB medium +ampicillin 100 μg/ml+avidin 0.2 U/ml).

The results observed are collated in Table 1:

TABLE 1

| Genotype of the E. coli strain | Amp. selection Transformants/μg of DNA | Selection on Amp medium + avidin 0.2 U/ml Transformants/μg of DNA |
|---|---|---|
| C268* Δ bioA, his | >$10^3$ (for each pool) | 3 (pool No. 4) 1 (pool No. 1) |
| C173* Δ bioD, his | >$10^3$ (for each pool) | 2 (pool No. 4) |

*Cleary and Campbell (1972) J. Bacteriol. 112, 830.

The plasmids are isolated from the clones selected on ampicillin+avidin and analyzed using restriction enzymes. Three plasmids (2 originating from the strain C268 and 1 from the strain C173) contain a 4.3-kb HindIII insert with a BglII site and 2 SphI sites and without a BamHI, SalI, PstI, EcoRV, PvuII or AvaI site.

With one of these plasmids, designated pTG1400, the restriction map of which is shown in FIG. 2, it is possible to retransform, by selecting for resistance to ampicillin and prototrophy for biotin, equally well the strains C268 (ΔbioA), C173(ΔbioD), R877(bioD19) (Cleary and Campbell, 1972) or C162(bioB) with an average frequency corresponding to that obtained for the selection with ampicillin alone (more than $10^3$ per μg of DNA). No complementation of the auxotrophy for biotin of the strains R878 (bioC23) or R901 (ΔbioA-D) (Cleary and Campbell, 1972) can be obtained using pTG1400.

b) In *Bacillus subtilis*

Complementation of the bio mutants of *Bacillus subtilis* could prove difficult since it is known that deletions can occur at a very high frequency in foreign inserts cloned into the usual replicative plasmids of *Bacillus subtilis*. A new strategy, based on complementation tests using a non-replicative plasmid, was thus developed. The integration of non-replicative plasmids in the genomic DNA of *Bacillus subtilis* takes place at a fairly high frequency (approximately $10^4$ transformants/pg of DNA), using naturally competent *Bacillus subtilis* cells, if there are homologous regions between the genomic DNA and the plasmid.

The first stage consists in integrating plasmid pTG475, whose structure is shown in FIG. 3, in different bio mutants of *Bacillus subtilis*.

Plasmid pTG475 contains the XylE gene which codes for the enzyme C 2,3-oxygenase [Zukowski et al. (1983) PNAS USA, 80, 1101–1105], which may be used as a chromogenic (yellow) marker and which is expressed under the control of the inducible promoter of the levansucrase gene of *Bacillus subtilis*. This plasmid also contains a CAT gene conferring resistance to chloramphenicol; the CAT and XylE genes are inserted into pBR322.

This plasmid is integrated in the chromosome of the following strains of *Bacillus subtilis*:
strain bioA: JKB 3173 [bioA 173, aro G932; CH Pai (1975) J. Bacteriol. 121, 1–8],
strain bioB: BGSC1A92 [bioB 141, aro G932 Sac A 321, Arg A2; CH Pai (1975) J. Bacteriol. 121 1–8],
strain bio112: JKB 3112 [bio 112; CH Pai (1975) J. Bacteriol. 121, 1–8],
by the competent cell transformation technique of R.J. Boyland (1972), J. Bacteriol. 110, 281–290, the selection being performed on TBAB (DIFCO Blood tryptose agar base) plus chloramphenicol 3 $\mu$g/ml.

Various checks are performed on the transformed clones: they turn yellow when induced with sucrose and, in addition, a check by Southern hybridization for the strains bioA, bioB and bio112 shows that integration of pTG475 by simple recombination in the promoter of the levansucrase gene has taken place. These transformed strains of *Bacillus subtilis* are referred to as bioA TG1, bioB TG2 and bio112 TG3. Since plasmid pTG475 has carried pBR322 sequences into the genome of *Bacillus subtilis*, it becomes possible to integrate, by homologous recombination, any foreign plasmid containing these same sequences.

In a second stage, plasmid pTG1400, previously cloned by complementation into *E. coli*, was used for transforming *Bacillus subtilis* strains bioA TG1, bioB TG2 and bio112 TG3. The selection is performed on LB medium +avidin 0.2 U/ml +chloramphenicol 10 $\mu$g/ml.

It is observed that it is possible to select, at a very high frequency, transformants which are prototrophic for biotin from strains bioA TG1 and bioB TG2 but not with the strain bio112 TG3. pTG1400 hence does not complement the bio112 mutation.

c) Final characterization of the HindIII insert . of pTG1400

Southern hybridization experiments were performed so as to detect the same HindIII fragment in the genomic DNA of *Bacillus sphaericus* IFO 3525, corresponding to the pTG1400 insert.

Under drastic hybridization conditions (50% formamide, 0.6% Denhardt's solution, 0.1% SDS, 3×SSC at 42° C.), and using a plasmid pTG1400 labelled with $^{32}$P by incorporation of radioactive nucleotides by in vitro polymerization (nick translation) (2.5×10$^7$ cpm/$\mu$g of DNA), a single 4.3-kb HindIII band could be visualized in the genomic DNA of *Bacillus sphaericus* IFO 3523 after 6 hours' autoradiography at $-80°$ C. It was verified that, under these hybridization conditions, pBR322 did not give a cross reaction with the genomic DNA of *Bacillus sphaericus* IFO 3525. Under these same conditions, no positive reaction, with pTG1400 as probe, could be detected in the HindIII-treated genomic DNA of *Bacillus subtilus* BGSC1A289 or in the HindIII treated genomic DNA of *E. coli* C600.

The whole DNA sequence of the 4.3-kb HindIII fragment was analyzed using the "Shotgun" method, that is to say the systematic cloning of the fragments obtained by sonication, or using "cyclone deletions" or elongation with oligonucleotide primers.

For the "shotgun" method, plasmid pTG1400 was broken up by ultrasound treatment. After treatment of the DNA segments with phage T$_4$ DNA polymerase, the blunt-ended fragments are allowed to migrate on a low-melting point agarose gel and fragments approximately 300 bp in size are isolated.

The cloning of these fragments is carried out in M13 vectors digested with SmaI and treated with phosphatase.

The clear plaques which do not give cross hybridization with pBR322 are screened and 100 clones are sequenced. The results were analyzed by computer.

A recent method for producing a series of overlapping clones (the cylone system) was used for sequencing the DNA [R.M.K. Dale, B.A. Mc Clure, J.P. Houchins (1985) Plasmid 13, 31–40]. This method was conducted in parallel with the "shotgun" method so as to confirm the results. In addition, this method produces defined deleted plasmids containing groups of bio genes or isolated bio genes.

The complete sequence of the HindIII fragment of pTG1400 is shown in FIGS. 4, 5, 6, 7 and 8.

Computer analysis of this sequence reveals that the fragment has the capacity to code for four long open reading-frames (LORF). The possible translation initiation sites and the Shine-Dalgarno regions are underlined. A palindromic region is underlined at the 5' end of the sequence which might represent a transcription termination site.

Detailed complementation analysis shows that the first LORF region (FIG. 5) (with 3 possible translation initiation sites) corresponds to the bioD gene.

Experiments known under the name of "maxicells" were carried out with *E. coli* strain CSR 603 (recA1, phr-1, uvrA6, thr-1, leu-6, thi-1, argE3, lacY1, galK2, ara14, xyl15, mtl1, proA2, str-31, tsx-33, supE44, F$^-$, lambda$^-$); they show that this region codes for a polypeptide with an apparent molecular weight of approximately 25 kd.

The second LORF region (FIG. 6) (with 4 possible translation initiation sites) corresponds to the bioA gene. A "maxicell" experiment with *E. coli* CSR603 reveals a polypeptide having an apparent molecular weight of approximately 40 kd which corresponds to the product of the bioA gene.

It was not possible to determine the function of the third LORF sequence, referred to as the Y gene (FIG. 7). A very great hydrophobicity and the presence of a probable signal sequence in the coding region suggest that this LORF, if it is transcribed and translated, codes for a protein that interacts with the membrane. The fact that this Y gene is in a cluster with the other bio genes (A, D and B) suggests that it codes for another function involved in biotin metabolism.

The fourth LORF region (FIG. 8) (with 3 possible translation initiation sites) has already been identified: it is a region coding for the bioB gene. It is demonstrated here that this gene is linked in a cluster with the bioA and bioD genes.

A complementation analysis with plasmids containing subcloned regions of the 4.3-kb HindIII insert of pTG1400 shows clearly, as is seen in FIG. 9, that the first LORF region corresponds to the product of the D gene and that the second LORF region corresponds to the product of the A gene.

EXAMPLE 2

Cloning by complementation of the bioF gene of
Bacillus sphaericus IFO 3525

The HindIII genomic DNA library of *Bacillus sphaericus* IFO 3525, described above, was used for transforming a mutant of *E. coli*, bioF 12, following the methodology described above.

The results obtained are collated in Table 2:

TABLE 2

| Genotype of the E. coli strain | Amp. selection Transformants/μg of DNA | Selection on Amp medium + avidin 0.2 U/ml Transformants/μg of DNA |
|---|---|---|
| R874* bioF 12, his | $>10^4$ (for each pool) | 2 (pool No. 1)<br>2 (pool No. 3)<br>4 (pool No. 4) |

*Cleary and Campbell (1972) J. Bacteriol. 112, 830

The plasmids are isolated from clones selected on medium containing ampicillin and avidin, and analyzed using restriction enzymes.

Two of these plasmids contain two approximately 4.5- and 0.6-kb HindIII inserts with SphI, KpnI, HpaI, NdeI, AvaI, ClaI, BglI, XmnI, PvuII, ScaI and StuI sites and without a BglII, XbaI, SmaI, PstI, SalI, NruI, BamHI, PvuI, EcoRI, HindII, EcoRV, FspI, ApaI, BalI or AatII, etc., site.

With one of these plasmids, Ptg1418, it was possible to retransform, by selecting for resistance to amoicillin and prototrophy for biotin, *E. coli* strain R874 (bioF12, his) with an average frequency corresponding to that obtained for the selection of the clones on ampicillin (more than $10^4/\mu g$ of DNA).

Subcloning experiments showed that only the 4.5-kb HindIII fragment codes for the KAPA synthetase function providing for the complementation of the bioF12 mutation of *E. coli* strain R874.

"Southern" experiments were performed so as to detect the 4.5-kb HindIII fragment in the genomic DNA of *Bacillus sphaericus* IFO 3525 compared with the 4.5-kb insert of pTG1418. Using very drastic hybridization conditions (50% formamide, 3×SSC, 0.1% SDS, 0.6% Denhardt's solution, 42° C.) and using M13TG1425 [phage M13 containing the 4.5-kb HindIII insert labelled with $^{32}P$ by incorporation of radioactive nucleotides by in vitro polymerization (nick translation) with $2\times10^6$ cpm/μg of DNA], an approximately 4.5-kb HindIII band may be visualized in the genomic DNA of *Bacillus sphaericus* IFO 3525 after 7 hours' autoradiography at −80° C.

Under the same conditions, no positive reaction can be detected either on the HindIII-treated genomic DNA of *Bacillus subtilis* BGSC1A289 or on the HindIII-treated genomic DNA of *E. coli* C600.

No cross reaction can be detected between the pTG1400 insert and pTG1418 inserts either with an 8.3-kb SphI fragment of pTG1406 overlapping the 3' end of pTG1400 or with an 8.2-kb MboI fragment of pSB01 overlapping the 5' end of pTG1400 (see FIG. 10).

The restriction map of the pTG1418 inserts was analyzed and is shown in FIG. 11.

Complementation studies and "Southern" analysis demonstrate that the bioF gene of *Bacillus sphaericus* IFO 3525 is not linked to the bioA, bioD and bioB genes of the same microorganism (FIG. 12).

EXAMPLE 3

Complementation of *B. subtilis* mutant bio112TG3 (derived from JBK 3112, bioC/F-112 aroG932) by integrative transformation with pTG1418 and different derivatives of the latter

*B. subtilis* mutant bio112 was identified by nutritional tests as being affected in the bioF or bioC function (C.H. Pai, 1975, J. Bacteriol 121, 1–8). In this mutant, plasmid pTG475 has been integrated at the level of the sacR - sacB locus following the methodology described above, the new strain thereby obtained being designated bio112 TG3.

Transformation of the strain bio112 TG3 by different plasmids (pTG1418, 1420, 1422, 1435, 1436 and 1437, shown in FIGS. 13 to 16) was performed, followed by selection on LB medium +chloramphenicol 10 μg/ml+avidin 500 U/1. The results of complementation are summarized in Table 3. Since the cross test with *E. coli* mutant R874(bioF, his) gives the same result, it is probable that *B. subtilis* mutant bio112 is affected in the bioF gene. By analyzing the complementations obtained in terms of the plasmids used, it is possible to localize the bioF gene on the pTG1418 insert at the level of a fragment bounded by the XmnI and NcoI restriction sites (see FIGS. 21 to 23).

TABLE 3

| Plasmid | Integrative transformation of B. subtilis strain bio112 TG3<br>Insert | Complementation on LB + 500 U/l avidin + 10 μg/ml chloramphenicol |
|---|---|---|
| pTG1418 | 5.1-kb HindIII insert | ++ |
| pTG1422 | 3.1-kb ClaI insert containing bioF and part of LORF W | ++ |
| pTG1420 | 2-kb ClaI-HindIII insert containing X and part of LORF W | − |
| pTG1436 | 1.3-kb XmnI-NcoI insert containing the bioF gene | ++ |
| pTG1437 | 1.3-kb NcoI-XmnI insert containing the bioF gene | ++ |
| pTG1435 | 0.6-kb HpaI-PvuII insert containing LORF X | − |

EXAMPLE 4

Nucleotide sequence of the 4.53-kb HindIII insert of plasmid pTG1418

The HindIII insert was cloned into M13TG131 at the level of the corresponding site of the polylinker. The so-called "cylone" method was applied to this plasmid M13TG1425 and the results were analyzed by computer. The few reading differences between the two complementary strands were elucidated on sequencing using specific oligonucleotides.

The sequence is given in detail in FIGS. 17 to 19. It is seen that this insert contains three open reading-frames coding, respectively, for proteins (subunits) of molecular weight 18,462, 28,048 and 42,940 daltons. The last gene, with respect to the reading direction, is localized in the region identified as bioF, the molecular weight of this B. sphaericus protein being of the same order of magnitude as that of E. coli KAPA synthetase (M.A. Eisenberg, 1973, adv. Enzymol. 38, 317–372).

The juxtaposition of these three open reading-frames might be, as in the case of the insert of plasmid pTG1400, typical of an operon structure. It should be noted that, upstream from the first gene, a 15-base pair sequence (underlined in FIG. 17) also present upstream from the first gene (bioD) of the insert of plasmid pTG1400 can be identified. This significant characteristic might indicate that the two groups of biotin genes of B. sphaericus are subjected at least to common regulation. The latter might correspond to control by biotin (or a derivative of the latter) as has already been described for the KAPA synthetase (bioF) of B. sphaericus (Y. Yzumi, K. Sato, Y. Tani and K. Ogata, 1973, Agric. Biol. Chem. 37, 1335).

On the 3' side of the last gene of the sequenced insert, a sequence possessing the characteristics of a transcription terminator may be identified (underlined in FIG. 18).

EXAMPLE 5

Complementation of E. coli mutants R878 (bioC, his) and C261 (ΔbioFCD, his), respectively, using plasmids pTG1418 (1433) and pTG1440

The traditional complementation methodology for bio mutants of E. coli are supplied using plasmid pTG1418 and different derivatives of the latter.

When competent cells of E. coli mutant R878 (bioC, his) are transformed with plasmids pTG1418 and pTG1433 (see Table 4), and then plated on LB medium+ampicillin 100 μg/ml+avidin 200 U/l growth is detected after 36 h of incubation at 37° C. The frequency of appearance of the transformed clones on this medium is of the same order of magnitude as that measured on LB medium +ampicillin 100 μg/ml.

TABLE 4

| Plasmid | Transformation of E. coli mutant R878 bioC Number of transformants per μg of DNA | |
|---|---|---|
| | Selection on LB medium + ampicillin (100 μg/ml) | Selection on LB medium + ampicillin + avidin (100 μg/ml) (200 U/l) |
| pTG1418 | $10^3$ | $10^3$ small |
| pTG1433 | $10^3$ | $10^3$ small |
| pBR322 | $10^3$ | 0 (after 36 h of incubation at 37° C.) |

The growth of the transformed clones, which are normal on LB+ampicillin, is retarded in the absence of biotin (LB medium+ampicillin+avidin; minimum plus casamino acids, devoid of biotin). This complementation of the biotin auxotrophy of the mutant R878 bioC is altogether significant, given the total absence of residual growth of this same mutant when it is transformed by various plasmids derived from pBR322 on medium devoid of biotin.

The two inserts of plasmids pTG1400 and pTG1418 were cloned into pBR322 to give plasmid pTG1440 (FIG. 20). This plasmid pTG1440, when introduced into E. coli mutant C261 (ΔbioFCD, his) enables clones to be selected on LB medium+ampicillin 100 μg/ml+avidin 200 U/1. The frequency of transformation obtained is directly comparable to that measured on LB+ampicillin. Again, the growth of these recombinant clones, which is normal on LB medium+ampicillin, is retarded in the absence of biotin. From these two results (complementation of the biotin auxotrophy of the mutant bioC and bio ΔFCD), it emerges clearly that the insert of plasmid pTG1418 also contains the bioC gene of B. sphaericus. The different subclonings derived from the pTG1418 insert (FIGS. 21 to 23) do not enable complementation of the bioC mutation of E. coli to be obtained. Only the inserts possessing all three genes confer effective complementation of the bioC mutation of E. coli.

EXAMPLE 6

Complementation of E. coli mutant bioH (PA505 MAΔ108, argH, metA, bioH, malA, str')

This mutant was originally described as bioB (D. Hatfield, M. Hofnung and M. Schwartz, 1969, J. Bacteriol. 98? 559-567). It was then characterized as not excreting any vitamer and as being capable of growth on inorganic medium in the presence of KAPA, DAPA, DTB or biotin. Eisenberg (1985, Annals New York Academy of Sciences 447, 335-349) then proposed that this gene codes for a subunit of pimeloyl-CoA synthetase (bioH). It should be noted that the E. coli mutants which are overproductive of biotin (selected either by a level of excretion of vitamin permitting the growth of a bioB auxotroph of E. coli, or by resistance to alpha-dehydrobiotin) have all been identified genetically as affected at the bioR locus. This locus codes for a multifunctional protein (repressor of the synthesis of the messenger RNAs of the bioABFCD operon and synthetase holoenzyme binding biotin to a lysine residue of different apoenzymes having a carboxylase function).

The fact that all the E. coli mutants which are overproductive of biotin identified to date are localized in the gene coding for the trans-active repressor and never in the operator of the bioABFCD operon suggests that another gene involved in biotin biosynthesis is subject to this regulation. From a review of the literature, the best candidate is the bioH gene.

Since the pTG1418 insert contains the bioF and bioC genes of B. sphaericus, an investigation was performed as to whether the third gene corresponded to bioH.

Complementation of the bioH mutant of E. coli was effectively obtained using plasmid pTG1433. Once again, the growth obtained on this medium is retarded, but is altogether significant compared with the controls (see Table 5).

TABLE 5

| Plasmid | Transformation of E. coli mutant bioH PA505 MAΔ08 Number of transformations per μg of DNA | |
|---|---|---|
| | Selection on LB medium + ampicillin (100 μg/ml) | Selection on LB medium + ampicillin + avidin (100 μg/ml) (200 U/l) |
| pBR322 | $10^4$ | 0 |
| pTG1433 | $10^3$ | $10^3$ small (after 36 h of incubation at 37° C.) |

As in the case of the complementation of the bioC mutant, a necessary and sufficient condition for complementation of the bioH mutant is the simultaneous presence of the three genes of the pTG1418 insert on the plasmids introduced into the strain (FIGS. 21 to 23).

In distinction to the bioF mutants of E. coli and B. subtilis, which are capable of being complemented by a single gene of B. sphaericus, growth of the bioC and bioH mutants of E. coli in the absence of biotin can hence be obtained only when recombinant plasmids carrying the three genes of the HindIII insert of pTG1418 are introduced. This might reflect, inter alia, differences in enzymatic properties between the pimeloyl-CoA synthetase of B. sphaericus and the corresponding enzyme of *E. coli* (difference in affinity towards the substrates, multienzyme edifice, in particular) or a reduced synthesis of pimeloyl-CoA synthetase of *B. sphaericus* in *E. coli*, limiting the metabolic flux of pimelate to KAPA.

EXAMPLE 7

The functional test of the bio FCH genes

The tests of complementation of the bioF, bioH and bioC mutants of *E. coli* using recombinant plasmids carrying inserts derived from the 4.5-kb HindIII fragement isolated from *B. sphaericus* may be recognized as evidence of the presence on this DNA of the bioF, bioH and bioC genes.

Nevertheless, it is useful to complement this information by a test of activity of the products of these genes cloned from *B. sphaericus.* The product of the bioF gene of *E. coli* was characterized as catalyzing the conversion of pimeloyl-CoA to KAPA (Eisenberg, 1968). The products of the two genes bioC and bioH are not clearly identified at the present time; a hypothesis mentioned in the literature (Eisenberg, 1985) suggests that they code for the proteins involved in the biosynthesis of pimeloylCoA. A test was performed to find out whether the bioF, C, H sequence provides specifically for the conversion of pimelate to KAPA.

The insert carrying the FCH coding portion of *B. sphaericus* (recovered in the form of an EcoRV-SphI fragment of pTG1434 in combination with the SphI-SphI fragment of pTG1436, ligated together) was fused to the promoter of the gene conferring resistance to tetracycline of pBR322 to give plasmid pTG1446, in order to obtain a significant level of expression of the proteins associated with the bioF, C and H genes.

This plasmid was then introduced into competent cells of *E. coli* strain bioH. This recombinant strain is then cultured at 37° C. for 48 hours in GP medium (for 1 liter: glycerol, 20 g; proteose peptone, 30 g; vitamin-free casamino acids, 5 g; $K_2HPO_4$, 1 g; KCl, 0.5 g; $MgSO_4.7H_2O$, 0.5 g; $FeSO_4.7H_2O$, 0.01 g; $MnSO_4.4H_2O$, 0.001 g, pH 6.8-7; thiamine-HCl, 20 μg) to which ampicillin 100 μg/ml and pimelate (pH 7.5) 0.5 mg/ml are added.

An aliquot of the supernatant (5 μl) is then chromatographed on a silica plate [chromato.solvent: n-butanol (60)/acetic acid (15)/water (25), vol/vol; migration of the solvent: 10 cm]so as to separate the vitamers and the biotin that are produced.

After migration specific to each vitamer, the KAPA is measured quantitatively by biological assay using a Saccharomyces cerevisiae collection strain, namely ATCC 7754.

Under these conditions, a quantity of 85 μg (expressed as biotin equivalents) of KAPA per ml of culture supernatant can be measured reproducibly.

The control in this experiment is the same strain containing plasmid pBR322, cultured under the same conditions. In this case, no significant detection of KAPA can be demonstrated.

It is hence shown here that the pTG1418 insert codes for the enzyme functions which are necessary and sufficient in the conversion of pimelate to KAPA, namely the products of the bioC, H and F genes.

Deposition of strains that are representative of the invention

*E. coli* strains C600 pTG1400 and R874 pTG1418 were deposited at the Collection Nationale de Cultures de Microorganismes (National Collection of Microorganisms Cultures) of the Institut Pasteur, 28 rue du Docteur-Roux - 75724 Paris Cedex 15, on 26 September 1986 under Nos. I-608 and I-609.

REFERENCES

P.P. Cleary and A. Campbell (1972) J. Bacteriol. 112, 830–839.

M.M. Zukowski, D.F. Gaffney, D. Speck, M. Kauffmann, A. Findeli, A. Wisecup and J.P. Lecocq (1983) PNAS USA 80, 1101–1105.

C.H. Pai (1975) J. Bacteriol. 121, 1-8.

R.J. Boyland, N.H. Mendelson, D. Brooks and F.E. Young (1972) J. Bacteriol. 110, 281–290.

R.M.K. Dale, B.A. Mc Clure and J.P. Houchins (1986) Plamid 13, 31–40.

S.N. Cohen, A.C.Y. Cheng and L. Hsu (1972) PNAS USA 69, 2110–2114.

H. Saito and K.I. Miura (1963) BBA 72, 619–629.

M.A. Eisenberg (1985) Regulation of the biotin operon. Annals New York Academy of Sciences, 447, 335–349.

M.A. Eisenberg and C. Star (1968) J. Bacteriol., 96, 1291–1297.

We claim:

1. A recombinant DNA molecule comprising a sequence encoding a gene product of *B. sphaericus,* wherein said sequence is selected from the group consisting of: (i) a sequence encoding the product of gene bio A, (ii) a sequence encoding the product of gene bioD, (iii) a sequence encoding the product of gene bio F, (iv) a sequence encoding the product of gene bio H, (v)( a sequence encoding the product of gene bio X, (vi) a sequence encoding the product of gene bio Y, and (viii) a sequence encoding the product of gene bio W.

2. A recombinant DNA molecule according to claim 1 wherein said molecule is devoid of natural sequences controlling the expression of said bio A, bio D, bio F, bio H, bio X, bio Y and bio W genes.

3. A cell comprising said recombinant DNA molecule according to claim 2.

4. The cell according to claim 3 wherein said cell is of the *E. coli* species.

5. The cell according to claim 3 wherein said cell is of the *B. sphaericus* species.

6. The recombinant molecule according to claim 1 wherein said molecule is a plasmid.

7. A cell of the *E. coli* species comprising said recombinant DNA molecule according to claim 1.

8. A cell of the *B. sphaericus* species comprising more than one copy of said recombinant DNA molecule according to claim 1.

9. A recombinant DNA molecule comprising, in any order, (i) a first open reading frame (ORF) encoding the product of gene bio D of *B. sphaericus,* (ii) a second ORF encoding the product of gene bio A of *B. sphaericus,* (iii) a third ORF encoding the product of gene bio Y of *B. sphaericus* and (iv) a fourth ORF encoding the product of gene bio B of *B. sphaericus.*

10. The recombinant DNA molecule according to claim 9 wherein said molecule comprises the 4.3 kb Hind III fragment of pTG14000.

11. A cell of the *E. coli* species comprising said recombinant DNA molecule according to claim 10.

12. The recombinant DNA molecule according to claim 9 wherein said first, second, third and fourth ORF's are devoid of natural sequences controlling the expression of said ORF's.

13. The recombinant molecule according to claim 9 wherein said molecule is a plasmid.

14. A cell of the *E. coli* species comprising said recombinant DNA molecule according to claim 9.

15. A recombinant DNA molecule comprising, in any order, (i) a first ORF encoding the product of gene bio X of *B. sphaericus*, (ii) a second ORF encoding the product of gene bio W of *B. sphaericus*, and (iii) a third ORF encoding the product of gene bio F of *B. sphaericus*.

16. The recombinant DNA molecule according to claim 15, wherein said molecule comprises the 4.5 kb Hind III fragment of pTG1418.

17. A cell of the *E. coli* species comprising said recombinant DNA molecule according to claim 16.

18. A cell of the *E. coli* species comprising said recombinant DNA molecule according to claim 15.

19. The recombinant DNA molecule according to claim 15 wherein said first, second and third ORF's are devoid of natural sequences controlling expression of said ORF's.

20. The recombinant molecule according to claim 15 wherein said molecule is a plasmid.

21. A plasmid selected from pTG1400 and pTG1418.

* * * * *